(12) United States Patent
Metcalf

(10) Patent No.: US 9,248,199 B2
(45) Date of Patent: Feb. 2, 2016

(54) 1:1 ADDUCTS OF SICKLE HEMOGLOBIN

(71) Applicant: Global Blood Therapeutics, Inc., South San Francisco, CA (US)

(72) Inventor: Brian W. Metcalf, South San Francisco, CA (US)

(73) Assignee: GLOBAL BLOOD THERAPEUTICS, INC., South San Francisco, CA (US)

( * ) Notice: Subject to any disclaimer, the term of this patent is extended or adjusted under 35 U.S.C. 154(b) by 69 days.

(21) Appl. No.: 14/167,632

(22) Filed: Jan. 29, 2014

(65) Prior Publication Data

US 2015/0209443 A1    Jul. 30, 2015

(51) Int. Cl.
*A61K 31/4155* (2006.01)
*A61K 31/5377* (2006.01)
*A61K 47/48* (2006.01)
*A61K 31/444* (2006.01)
*A61K 31/4439* (2006.01)
*A61K 31/5386* (2006.01)

(52) U.S. Cl.
CPC ....... *A61K 47/48307* (2013.01); *A61K 31/4155* (2013.01); *A61K 31/444* (2013.01); *A61K 31/4439* (2013.01); *A61K 31/5377* (2013.01); *A61K 31/5386* (2013.01)

(58) Field of Classification Search
None
See application file for complete search history.

(56) References Cited

U.S. PATENT DOCUMENTS

| 2013/0190315 A1 | 7/2013 | Metcalf et al. |
| 2013/0190316 A1 | 7/2013 | Metcalf et al. |
| 2014/0271591 A1 * | 9/2014 | Sinha ................. A61K 31/4439 424/93.73 |

FOREIGN PATENT DOCUMENTS

| JP | 2003-075970 A | 3/2003 |
| WO | WO-2007/084914 A2 | 7/2007 |

OTHER PUBLICATIONS

Abdulmalik, O. et al., "Crystallographic analysis of human hemoglobin elucidates the structural basis of the potent and dual antisickling activity of pyridyl derivatives of vanillin." Acta Cryta. 2011, D67, pp. 920-928.

Luan et al., "TOPS-MODE model of multiplexing neuroprotective effects of drugs and experimental-theoretic study of new 1,3-rasagiline derivatives potentially useful in neurodegenerative disease," Bioorganic & Medicinal Chemistry, (2013) 21:1870-1879.

PCT International Search Report and Written Opinion dated Oct. 31, 2014 in PCT Patent Application No. PCT/US2014/013575.

Safo et al., "Structural basis for the potent antisickling effect of a novel class of five-membered heterocyclic aldehydic compounds," J Med Chem, 2004, 47(19):4665-76.

* cited by examiner

*Primary Examiner* — Kamal Saeed
(74) *Attorney, Agent, or Firm* — Foley & Lardner LLP

(57) ABSTRACT

Provide herein are 1:1 adducts of sickle hemoglobin (HbS) and a compound of formula (I), as defined herein, suitable as modulators of HbS, and methods for their use in treating disorders mediated by hemoglobin and disorders that would benefit from tissue and/or cellular oxygenation.

2 Claims, 3 Drawing Sheets

A  B

1:1 ADDUCTS OF SICKLE HEMOGLOBIN

FIELD OF THE INVENTION

This invention provides 1:1 adducts, of sickle hemoglobin (HbS) and a compound of formula (I), as defined herein, suitable as modulators of HbS, and methods for their use in treating disorders mediated by HbS as well as disorders that would benefit from tissue and/or cellular oxygenation.

STATE OF THE ART

Sickle cell disease is a disorder of the red blood cells, found particularly among those of African and Mediterranean descent. The basis for sickle cell disease is found in sickle hemoglobin (HbS), which contains a point mutation relative to the prevalent peptide sequence of hemoglobin (Hb).

Hemoglobin (Hb) transports oxygen molecules from the lungs to various tissues and organs throughout the body. Hemoglobin binds and releases oxygen through conformational changes. Sickle hemoglobin (HbS) contains a point mutation where glutamic acid is replaced with valine, allowing HbS to become susceptible to polymerization to give the HbS containing red blood cells their characteristic sickle shape. The sickled cells are also more rigid than normal red blood cells, and their lack of flexibility can lead to blockage of blood vessels.

Some five-membered aldehydes, including furfural (FUF) and 5-hydroxymethyl-2-furfural (5HMF), have been shown to increase the oxygen affinity of HbS and inhibit the sickling of homozygous sickle red blood (SS) cells. It has been reported that these aldehydes, such as FUF and 5HMF, act by forming Schiff bases with HbS. Specifically, two molecules of FUF or 5HMF bind to each HbS protein by forming two Schiff base adducts, in a symmetry-related fashion, at the R-cleft at the two N-terminal RVal1 residues of the HbS protein. See e.g., M. K. Safo et al., *J. Med. Chem.* 2004, 47, 4665-4676 and O. Abdulmalik et al., *Acta Cryst.* 2011, D67, 920-928. Due at least in part to the enormous quantity of HbS protein that must be modified in a patient and the need to form a 2:1 aldehyde compound: HbS adducts with HbS protein, these aldehydes are generally administered at doses that are unacceptably high and potentially toxic.

SUMMARY OF THE INVENTION

This invention relates generally to 1:1 adducts comprising sickle hemoglobin (HbS) and a compound of formula (I), as described below. The 1:1 adducts are more suitable than 2:1 adducts as allosteric modulators of hemoglobin because the compounds of formula (I) can be administered at effective doses that are lower and potentially safer than doses of compounds that form 2:1 adducts with HbS. Without being bound by theory, it is contemplated that the binding of the compounds of formula (I) to HbS forms a conformationally stable 1:1 adduct. The conformation of that adduct does not require a second compound of formula (I) to bind to HbS. Moreover, the 1:1 adduct so formed inhibits formation of the sickled configuration of HbS in vivo. In some embodiments, the 1:1 adduct is isolated. Binding of the compound of formula (I) to HbS may be reversible or irreversible. When binding is reversible, each compound of formula (I) generally forms reversible 1:1 adducts with multiple HbS proteins. When binding is irreversible, each compound of formula (I) generally forms irreversible 1:1 adducts with a single HbS protein. In some aspects, this invention relates to methods for dosing a subject and treating disorders mediated by hemoglobin and disorders that would benefit from tissue and/or cellular oxygenation, where the methods are predicted on the formation of a 1:1 adduct comprising sickle hemoglobin (HbS) and a compound of formula (I).

In certain aspects of the invention, provided is a 1:1 adduct of sickle hemoglobin (HbS) and a compound of formula (I):

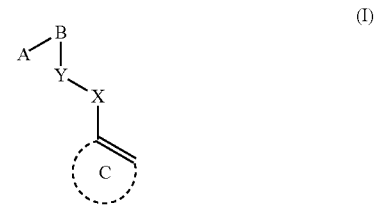

or a pharmaceutically acceptable salt of the compound, wherein

X is $CH_2$ or O;
Y is $CH_2$ or O;
A is:

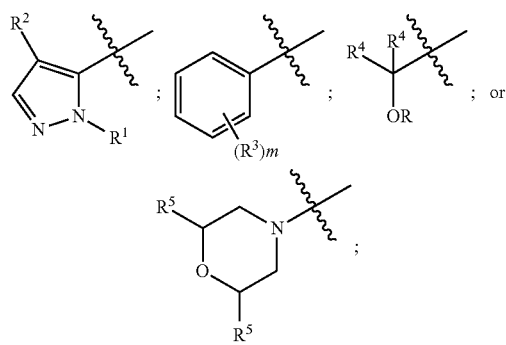

wherein
R is hydrogen or $C_1$-$C_6$ alkyl;
$R^1$ is hydrogen, $C_1$-$C_6$ alkyl optionally substituted with 3-6 fluoro atoms or with $-CO_2R^{2a}$;
$R^2$ is hydrogen or $C_1$-$C_6$ alkyl;
$R^{2a}$ is hydrogen or $C_1$-$C_6$ alkyl;
$R^3$ is $C_1$-$C_6$ alkyl;
each $R^4$ independently is hydrogen or $C_1$-$C_6$ alkyl;
each $R^5$ independently is hydrogen or $C_1$-$C_6$ alkyl, or both $R^5$ are $C_1$ alkyl joined to form a $-CH_2CH_2-$ moiety that combines with the carbon and oxygen atoms to which they are joined to form a five-membered heterocyclic ring;
m is 0, 1, 2, 3 or 4;
B is:

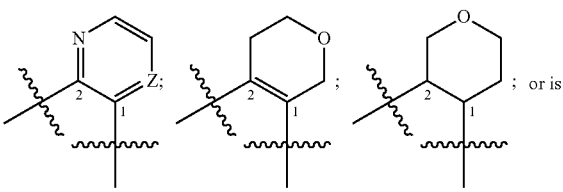

-continued

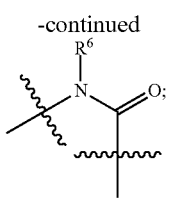

wherein
preferably the 2 position is joined with A;
Z is CH or N;
$R^6$ is hydrogen or $C_1$-$C_6$ alkyl;
C is:

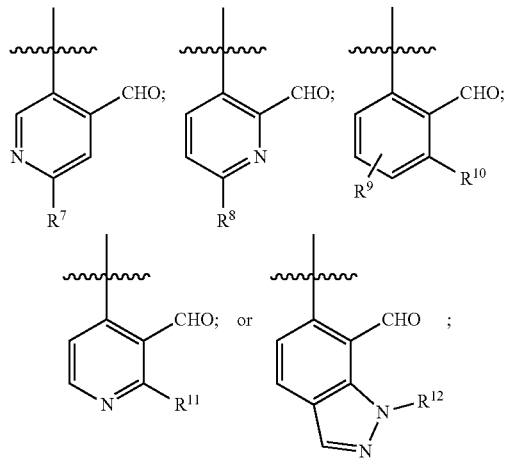

wherein
$R^7$ is hydrogen, $C_1$-$C_6$ alkyl; OH, or O—$C_1$-$C_6$ alkyl, optionally substituted with a 5- to 6-membered heterocycle containing at least 1 oxygen and/or nitrogen moiety;
$R^8$ is hydrogen, $C_1$-$C_6$ alkyl; OH, or O—$C_1$-$C_6$ alkyl; $R^9$ is hydrogen, $C_1$-$C_6$ alkyl; OH, or O—$C_1$-$C_6$ alkyl;
$R^{10}$ is hydrogen, $C_1$-$C_6$ alkyl; OH, or O—$C_1$-$C_6$ alkyl;
$R^{11}$ is hydrogen, $C_1$-$C_6$ alkyl or $N(R^{13})_2$;
$R^{12}$ is hydrogen or $C_1$-$C_6$ alkyl; and
each $R^{13}$ independently is hydrogen or $C_1$-$C_6$ alkyl.

In further aspects of the invention, a method is provided for dosing a subject with a compound of formula (I), comprising administering an effective dosage of the compound of formula (I), wherein the effective dosage is predicated on the formation of a 1:1 adduct between the compound of formula (I) and sickle hemoglobin (HbS) in the subject. In some embodiments, the 1:1 adduct is formed in the presence of excess compound of formula (I) that is not bound to HbS. Formation of the conformationally stable 1:1 adduct is advantageous because it does not require a second compound of formula (I) to bind to HbS and thus the dosage of the compound of formula (I) can be lowered to concentrations that safer than concentrations needed to form 2:1 adducts with HbS. Moreover, the 1:1 adduct so formed inhibits formation of the sickled configuration of HbS in vivo.

In further aspects of the invention, a method is provided of forming a 1:1 adduct of sickle hemoglobin (HbS) and a compound of formula (I), as claimed in any one of claims 1-5, comprising contacting the HbS with the compound of formula (I) under conditions wherein said adduct is formed.

In a further aspects of the invention, a method is provided for inhibiting sickling of HbS in a patient which method comprises administering to said patient a sufficient amount of a composition comprising a compound of formula (I) so as to form in vivo a 1:1 adduct with HbS thereby inhibiting sickling of HbS.

In still further aspects of the invention, a method is provided for increasing oxygen affinity of sickle hemoglobin (HbS) comprising contacting the HbS with a compound of formula (I), as claimed in any one of claims 1-5, to convert at a part to substantially all of the HbS to form a 1:1 adduct with the compound of formula (I) and allowing that adduct to bind to oxygen.

DETAILED DESCRIPTION OF THE INVENTION

Figure 1:
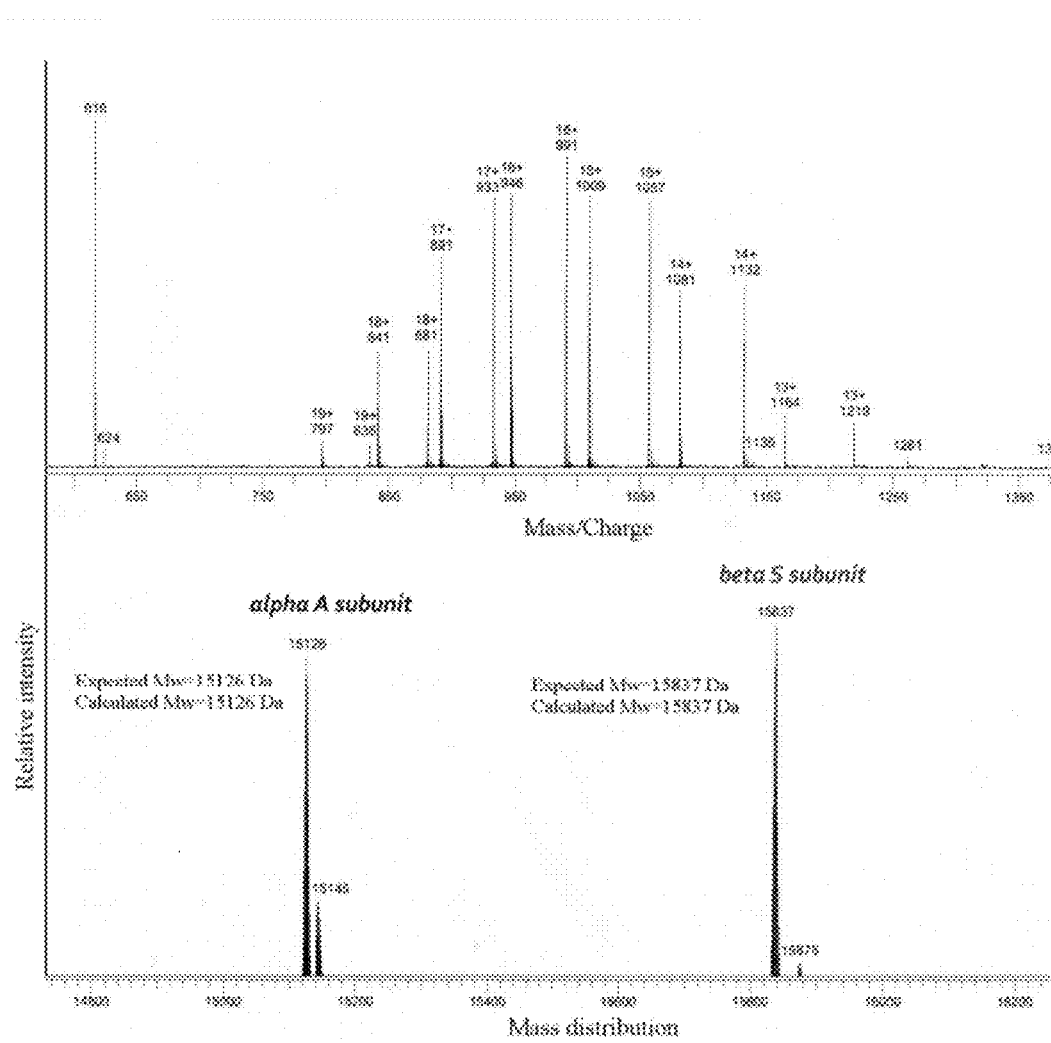
FIG. 1 depicts the ESI-MS spectrum of human hemoglobin S.

It must be noted that as used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques. The term "about" when used before a numerical designation, e.g., temperature, time, amount, and concentration, including range, indicates approximations which may vary by (+) or (−) 10%, 5% or 1%.

As used herein, Cm-Cn, such as C1-C12, C1-C8, or C1-C6 when used before a group refers to that group containing m to n carbon atoms.

The term "alkoxy" refers to —O-alkyl.
The term "alkyl" refers to monovalent saturated aliphatic hydrocarbyl groups having from 1 to 12 carbon atoms (i.e., C1-C12 alkyl) or 1 to 8 carbon atoms (i.e., C1-C8 alkyl), or 1 to 4 carbon atoms. This term includes, by way of example, linear and branched hydrocarbyl groups such as methyl (CH3-), ethyl (CH3CH2-), n-propyl (CH3CH2CH2-), iso-propyl ((CH3)2CH—), n-butyl (CH3CH2CH2CH2-), isobutyl ((CH3)2CHCH2-), sec-butyl ((CH3)(CH3CH2)CH—), t-butyl ((CH3)3C—), n-pentyl (CH3 CH2CH2CH2CH2-), and neopentyl ((CH3)3CCH2-).

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom. For example, and without limitation, the following is an aryl group:

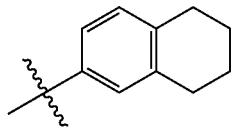 [SMILES: *c1ccc2c(c1)CCCC2]

The term "—CO$_2$H ester" refers to an ester formed between the —CO$_2$H group and an alcohol, preferably an aliphatic alcohol. A preferred example included —CO$_2$R$^E$, wherein R$^E$ is alkyl or aryl group optionally substituted with an amino group.

The term "chiral moiety" refers to a moiety that is chiral. Such a moiety can possess one or more asymmetric centers. Preferably, the chiral moiety is enantiomerically enriched, and more preferably a single enantiomer. Non limiting examples of chiral moieties include chiral carboxylic acids, chiral amines, chiral amino acids, such as the naturally occurring amino acids, chiral alcohols including chiral steroids, and the likes.

The term "cycloalkyl" refers to a monovalent, preferably saturated, hydrocarbyl mono-, bi-, or tricyclic ring having 3-12 ring carbon atoms. While cycloalkyl, refers preferably to saturated hydrocarbyl rings, as used herein, it also includes rings containing 1-2 carbon-carbon double bonds. Nonlimiting examples of cycloalkyl include cyclopropyl, cyclobutyl, cyclopentyl, cyclohexyl, cycloheptyl, adamentyl, and the like. The condensed rings may or may not be non-aromatic hydrocarbyl rings provided that the point of attachment is at a cycloalkyl carbon atom. For example, and without limitation, the following is a cycloalkyl group:

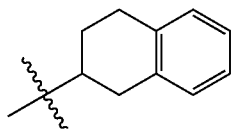 [SMILES: *C1CCc2ccccc2C1]

The term "halo" refers to F, Cl, Br, and/or I.

The term "heteroaryl" refers to a monovalent, aromatic mono-, bi-, or tricyclic ring having 2-16 ring carbon atoms and 1-8 ring heteroatoms selected preferably from N, O, S, and P and oxidized forms of N, S, and P, provided that the ring contains at least 5 ring atoms. Nonlimiting examples of heteroaryl include furan, imidazole, oxadiazole, oxazole, pyridine, quinoline, and the like. The condensed rings may or may not be a heteroatom containing aromatic ring provided that the point of attachment is a heteroaryl atom. For example, and without limitation, the following is a heteroaryl group:

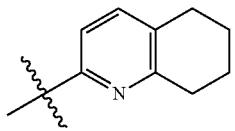 [SMILES: *c1ccc2c(n1)CCCC2]

The term "heterocyclyl" or heterocycle refers to a non-aromatic, mono-, bi-, or tricyclic ring containing 2-12 ring carbon atoms and 1-8 ring heteroatoms selected preferably from N, O, S, and P and oxidized forms of N, S, and P, provided that the ring contains at least 3 ring atoms. While heterocyclyl preferably refers to saturated ring systems, it also includes ring systems containing 1-3 double bonds, provided that they ring is non-aromatic. Nonlimiting examples of heterocyclyl include, azalactones, oxazoline, piperidinyl, piperazinyl, pyrrolidinyl, tetrahydrofuranyl, and tetrahydropyranyl. The condensed rings may or may not contain a non-aromatic heteroatom containing ring provided that the point of attachment is a heterocyclyl group. For example, and without limitation, the following is a heterocyclyl group:

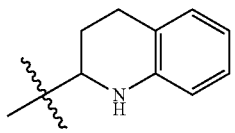 [SMILES: *C1CCc2ccccc2N1]

The term "oxo" refers to a C=O group, and to a substitution of 2 geminal hydrogen atoms with a C=O group.

The term "optionally substituted" refers to a substituted or unsubstituted group. The group may be substituted with one or more substituents, such as e.g., 1, 2, 3, 4 or 5 substituents. Preferably, the substituents are selected from the group consisting of oxo, halo, —CN, NO$_2$, —N$_2$+, —CO$_2$R$^{100}$, —OR$^{100}$, —SR$^{100}$, —SOR$^{100}$, —SO$_2$R$^{100}$, —NR$^{101}$R$^{102}$, —CONR$^{101}$R$^{102}$, —SO$_2$NR$^{101}$R$^{102}$, C$_1$-C$_6$ alkyl, C$_1$-C$_6$ alkoxy, —CR$^{100}$=C(R$^{100}$)$_2$, —CCR$^{100}$, C$_3$-C$_{10}$ cycloalkyl, C$_3$-C$_{10}$ heterocyclyl, C$_6$-C$_{12}$ aryl and C$_2$-C$_{12}$ heteroaryl, wherein each R$^{100}$ independently is hydrogen or C$_1$-C$_8$ alkyl; C$_3$-C$_{12}$ cycloalkyl; C$_3$-C$_{10}$ heterocyclyl; C$_6$-C$_{12}$ aryl; or C$_2$-C$_{12}$ heteroaryl; wherein each alkyl, cycloalkyl, heterocyclyl, aryl, or heteroaryl is optionally substituted with 1-3 halo, 1-3 C$_1$-C$_6$ alkyl, 1-3 C$_1$—C6 haloalkyl or 1-3 C$_1$-C$_6$ alkoxy groups. Preferably, the substituents are selected from the group consisting of chloro, fluoro, —OCH$_3$, methyl, ethyl, iso-propyl, cyclopropyl, vinyl, ethynyl, —CO$_2$H, —CO$_2$CH$_3$, —OCF$_3$, —CF$_3$ and —OCHF$_2$.

The term "adduct" refers to a composition formed between a compound and hemoglobin, preferably HbS, which is characterized and/or observed by physico chemical methods, and/or isolated. Such a composition can involve non-covalent interactions and/or covalent bond formation between HbS and the compound participating in the adduct. The adducts can form reversibly or irreversibly.

R$^{101}$ and R$^{102}$ independently is hydrogen; C$_1$-C$_8$ alkyl, optionally substituted with —CO$_2$H or an ester thereof, C$_1$-C$_6$ alkoxy, oxo, —CR$^{103}$=C(R$^{103}$)$_2$, —CCR, C$_3$-C$_{10}$ cycloalkyl, C$_3$-C$_{10}$ heterocyclyl, C$_6$-C$_{12}$ aryl, or C$_2$-C$_{12}$ heteroaryl, wherein each R$^{103}$ independently is hydrogen or C$_1$-C$_8$ alkyl; C$_3$-C$_{12}$ cycloalkyl; C$_3$-C$_{10}$ heterocyclyl; C$_6$-C$_{12}$ aryl; or C$_2$-C$_{12}$ heteroaryl; wherein each cycloalkyl, heterocyclyl, aryl, or heteroaryl is optionally substituted with 1-3 alkyl groups or 1-3 halo groups, or $R^{101}$ and $R^{102}$ together with the nitrogen atom they are attached to form a 5-7 membered heterocycle.

The term "pharmaceutically acceptable" refers to safe and non-toxic for in vivo, preferably, human administration.

The term "pharmaceutically acceptable salt" refers to a salt that is pharmaceutically acceptable.

The term "salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionally, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisalfate, mono-, di-, and tribasic phosphate, mesylate, tosylate, and the likes.

The terms "treat", "treating" or "treatment", as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting or suppressing the development of the disease or condition, relieving the disease or condition, causing regression of the disease or condition, relieving a condition caused by the disease or condition, or suppressing the symptoms of the disease or condition, and are intended to include prophylaxis. The terms also include relieving the disease or conditions, e.g., causing the regression of clinical symptoms. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "preventing" or "prevention" refer to a reduction in risk of acquiring a disease or disorder (i.e., causing at least one of the clinical symptoms of the disease not to develop in a subject that may be exposed to or predisposed to the disease but does not yet experience or display symptoms of the disease). The terms further include causing the clinical symptoms not to develop, for example in a subject at risk of suffering from such a disease or disorder, thereby substantially averting onset of the disease or disorder.

The term "effective amount" refers to an amount that is effective for the treatment of a condition or disorder by an intranasal administration of a compound or composition described herein. In some embodiments, an effective amount of any of the compositions or dosage forms described herein is the amount used to treat a disorder mediated by hemoglobin or a disorder that would benefit from tissue and/or cellular oxygenation of any of the compositions or dosage forms described herein to a subject in need thereof. In some embodiments, for example and without limitation, related to methods of forming a 1:1 adduct or of increasing oxygen affinity of HbS, an effective amount of the compound utilized herein is contacted with HbS.

The term "carrier" as used herein, refers to relatively non-toxic chemical compounds or agents that facilitate the incorporation of a compound into cells, e.g., red blood cells, or tissues.

1:1 Adducts of HbS

In certain aspects of the invention, provided is a 1:1 adduct of sickle hemoglobin (HbS) and a compound of formula (I):

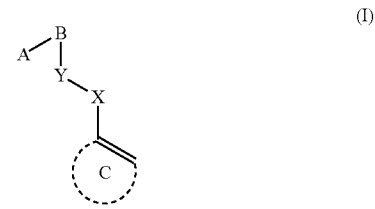

or a pharmaceutically acceptable salt of the compound, wherein

X is $CH_2$ or O;

Y is $CH_2$ or O;

A is:

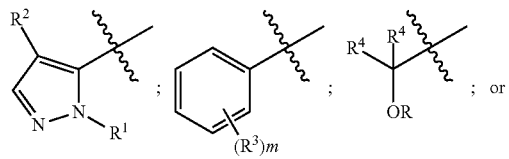

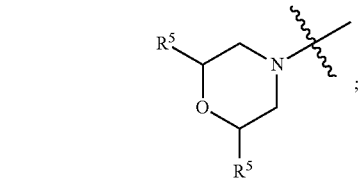

wherein

R is hydrogen or $C_1$-$C_6$ alkyl;

$R^1$ is hydrogen, $C_1$-$C_6$ alkyl optionally substituted with 3-6 fluoro atoms or with —$CO_2R^{2a}$;

$R^2$ is hydrogen or $C_1$-$C_6$ alkyl;

$R^{2a}$ is hydrogen or $C_1$-$C_6$ alkyl;

$R^3$ is $C_1$-$C_6$ alkyl;

each $R^4$ independently is hydrogen or $C_1$-$C_6$ alkyl;

each $R^5$ independently is hydrogen or $C_1$-$C_6$ alkyl, or both $R^5$ are $C_1$ alkyl joined to form a —$CH_2CH_2$— moiety that combines with the carbon and oxygen atoms to which they are joined to form a five-membered heterocyclic ring;

m is 0, 1, 2, 3 or 4;

B is

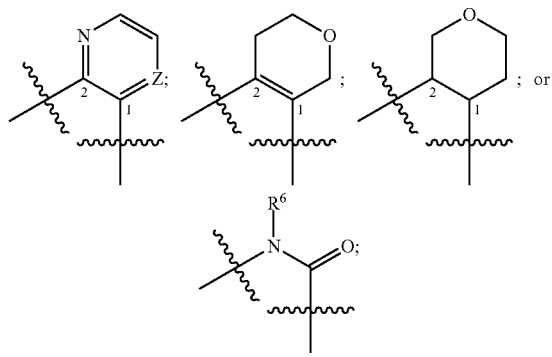

wherein

Z is CH or N;

$R^6$ is hydrogen or $C_1$-$C_6$ alkyl;

C is:

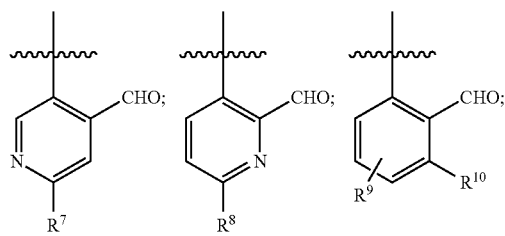

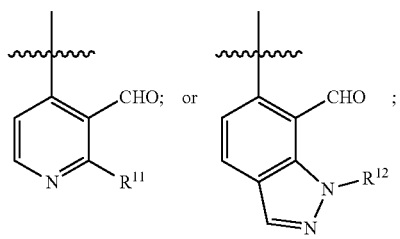

wherein $R^7$ is hydrogen, $C_1$-$C_6$ alkyl; OH, or O—$C_1$-$C_6$ alkyl, optionally substituted with a 5- to 6-membered heterocycle containing at least 1 oxygen and/or nitrogen moiety;

$R^8$ is hydrogen, $C_1$-$C_6$ alkyl; OH, or O—$C_1$-$C_6$ alkyl;

$R^9$ is hydrogen, $C_1$-$C_6$ alkyl; OH, or O—$C_1$-$C_6$ alkyl;

$R^{10}$ is hydrogen, $C_1$-$C_6$ alkyl; OH, or O—$C_1$-$C_6$ alkyl;

$R^{11}$ is hydrogen, $C_1$-$C_6$ alkyl or $N(R^{13})_2$;

$R^{12}$ is hydrogen or $C_1$-$C_6$ alkyl; and each $R^{13}$ independently is hydrogen or $C_1$-$C_6$ alkyl.

In certain preferred embodiments, X is $CH_2$ and Y is O. In some embodiments, X is O and Y is $CH_2$.

In certain preferred embodiments, A is

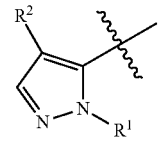

$R^1$, for example, may be hydrogen. $R^1$ may be $C_1$-$C_6$ alkyl, such as methyl, ethyl, n-propyl, iso-propyl or butyl. $R^1$ may be $C_1$-$C_6$ alkyl substituted with 3-6 fluoro atoms, such as —$CH_2CHF_2$, —$CH_2CF_3$, or —$CH_2CH_2CF_3$. $R^1$ may be —$CO_2R^{2a}$, such as —$CH_2CO_2H$. $R^2$ may be hydrogen. Alternatively, $R^2$ may be $C_1$-$C_6$ alkyl such as methyl, ethyl, n-propyl, iso-propyl or butyl.

In other preferred embodiments, A is

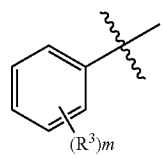

Substituent $R^3$, for example, may be $C_1$-$C_6$ alkyl, such as methyl, ethyl, n-propyl, iso-propyl or butyl. The variable m may be 0, 1, 2, 3 or 4.

In some embodiments, A is

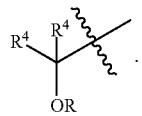

Substituent R, for example, may be hydrogen. Alternatively, R may be $C_1$-$C_6$ alkyl, such as methyl, ethyl, n-propyl, iso-propyl or butyl. Each $R^4$ independently may be hydrogen. Alternatively, each $R^4$ independently may be $C_1$-$C_6$ alkyl, such as methyl, ethyl, n-propyl, iso-propyl or butyl.

In some embodiments, A is

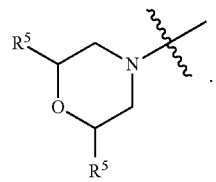

Each $R^5$ for example, may be hydrogen. $R^5$ may be $C_1$-$C_6$ alkyl, such as methyl, ethyl, n-propyl, iso-propyl or butyl. Alternatively, both $R^5$ are $C_1$ alkyl joined to form a —$CH_2CH_2$-moiety that combines with the carbon and oxygen atoms to which they are joined to form the following five-membered heterocyclic ring In certain preferred embodiments, B is

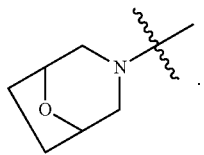 [SMILES: *N1CC2CCC(C1)O2]

In some embodiments, B is

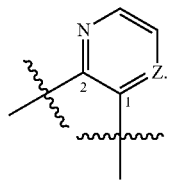

In certain preferred embodiments, Z is CH. In some embodiments, Z is N.

In some embodiments, B is

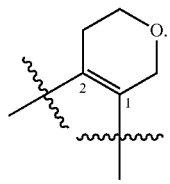 [SMILES: *C1=C(*)COCC1]

In some embodiments, B is

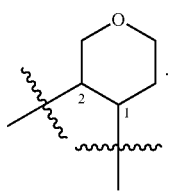 [SMILES: *C1CCOCC1*]

In some embodiments, B is

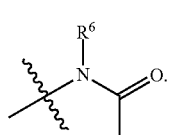

In certain preferred embodiments, $R^6$ is hydrogen. In some embodiments, $R^6$ is $C_1$-$C_6$ alkyl such as methyl, ethyl, n-propyl, iso-propyl or butyl.

In certain preferred embodiments, ring C is

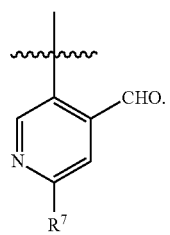

In some embodiments, $R^7$ is hydrogen. In some embodiments, $R^7$ is $C_1$-$C_6$ alkyl such as methyl, ethyl, n-propyl, iso-propyl or butyl. In some embodiments, $R^7$ is OH. In some embodiments, $R^7$ is O—$C_1$-$C_6$ alkyl such as $OCH_3$, $OCH_2CH_3$, $OCH_2CH_2CH_3$, $OCHCH_3CH_3$ or O-butyl, optionally substituted with a 5- to 6-membered heterocycle containing at least 1 oxygen and/or nitrogen moiety. In some preferred embodiments, $R^7$ is $OCH_3$. In some embodiments, $R^7$ is

In some embodiments, ring C is

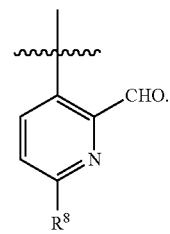

In some embodiments, $R^8$ is hydrogen. In some embodiments, $R^8$ is $C_1$-$C_6$ alkyl such as methyl, ethyl, n-propyl, iso-propyl or butyl. In some embodiments, $R^8$ is OH. In some embodiments, $R^8$ is O—$C_1$-$C_6$ alkyl such as $OCH_3$, $OCH_2CH_3$, $OCH_2CH_2CH_3$, $OCHCH_3CH_3$ or O-butyl, optionally substituted with a 5- to 6-membered heterocycle containing at least 1 oxygen and/or nitrogen moiety. In some preferred embodiments, $R^8$ is $OCH_3$.

In certain preferred embodiments, ring C is

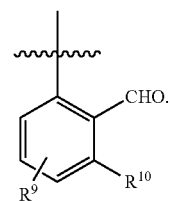

In some embodiments, $R^9$ is hydrogen. In some embodiments, $R^9$ is $C_1$-$C_6$ alkyl such as methyl, ethyl, n-propyl, iso-propyl or butyl. In some embodiments, $R^9$ is OH. In some embodiments, $R^9$ is O—$C_1$-$C_6$ alkyl such as $OCH_3$, $OCH_2CH_3$, $OCH_2CH_2CH_3$, $OCHCH_3CH_3$ or O-butyl, optionally substituted. In some preferred embodiments, $R^9$ is $OCH_3$.

In some embodiments, $R^{10}$ is hydrogen. In some embodiments, $R^{10}$ is $C_1$-$C_6$ alkyl such as methyl, ethyl, n-propyl, iso-propyl or butyl. In some preferred embodiments, $R^{10}$ is OH. In some embodiments, $R^8$ is O—$C_1$-$C_6$ alkyl such as $OCH_3$, $OCH_2CH_3$, $OCH_2CH_2CH_3$, $OCHCH_3CH_3$ or O-butyl, optionally substituted. In some preferred embodiments, $R^{10}$ is $OCH_3$.

In some embodiments, ring C is

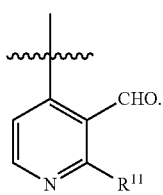

In some embodiments, $R^{11}$ is hydrogen. In some embodiments, $R^{11}$ is $C_1$-$C_6$ alkyl such as methyl, ethyl, n-propyl, iso-propyl or butyl. In some embodiments, $R^{11}$ is $NH_2$. In some embodiments, $R^{11}$ is $NMe_2$. In some embodiments, $R^{13}$ is hydrogen. In some embodiments, $R^{13}$ is $C_1$-$C_6$ alkyl such as methyl, ethyl, n-propyl, iso-propyl or butyl.

In some embodiments, ring C is

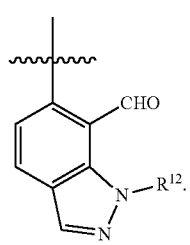

In some embodiments, $R^{12}$ is hydrogen. In some embodiments, $R^{12}$ is $C_1$-$C_6$ alkyl such as methyl, ethyl, n-propyl, iso-propyl or butyl.

In some embodiments of the 1:1 adduct,

R is hydrogen;

$R^1$ is methyl, ethyl, iso-propyl, —$CH_2CHF_2$, —$CH_2CF_3$, —$CH_2CH_2CF_3$, or —$CH_2CO_2H$;

$R^2$ is methyl or hydrogen;

$R^3$ is methyl and m is 1;

$R^4$ is methyl;

both $R^5$ are joined to form a —$CH_2CH_2$— moiety;

$R^7$ is $OCH_3$, OH, or

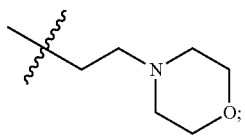 [SMILES: *CCN1CCOCC1]

$R^8$ is methyl;

$R^9$ is hydrogen $R^{10}$ is hydrogen or OH;

$R^{11}$ is $NH_2$; and $R^{12}$ is hydrogen.

In other embodiments of the 1:1 adduct, the compound of formula (I) is of formula (II):

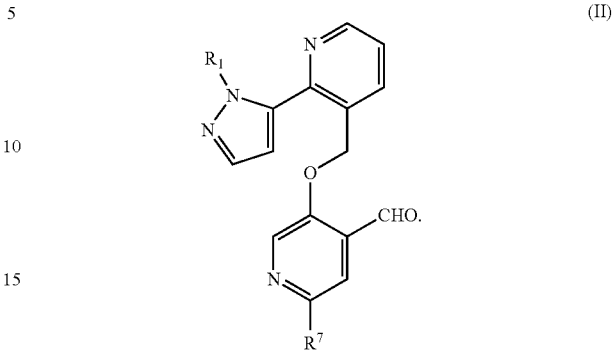

In some embodiments, $R^1$, for example, may be hydrogen. $R^1$ may be $C_1$-$C_6$ alkyl, such as methyl, ethyl, n-propyl, iso-propyl or butyl. $R^1$ may be $C_1$-$C_6$ alkyl substituted with 3-6 fluoro atoms, such as —$CH_2CHF_2$, —$CH_2CF_3$, or —$CH_2CH_2CF_3$. $R^1$ may be —$CO_2R^{2a}$, such as —$CH_2CO_2H$. $R^2$ may be hydrogen. Alternatively, $R^2$ may be $C_1$-$C_6$ alkyl such as methyl, ethyl, n-propyl, iso-propyl or butyl.

In some embodiments, $R^7$ is hydrogen. In some embodiments, $R^7$ is $C_1$-$C_6$ alkyl such as methyl, ethyl, n-propyl, iso-propyl or butyl. In some embodiments, $R^7$ is OH. In some embodiments, $R^7$ is O—$C_1$-$C_6$ alkyl such as $OCH_3$, $OCH_2CH_3$, $OCH_2CH_2CH_3$, $OCHCH_3CH_3$ or O-butyl, optionally substituted with a 5- to 6-membered heterocycle containing at least 1 oxygen and/or nitrogen moiety. In some preferred embodiments, $R^7$ is $OCH_3$. In some embodiments, $R^7$ is

In other embodiments of the 1:1 adduct, the compound of formula (I) is of formula (III):

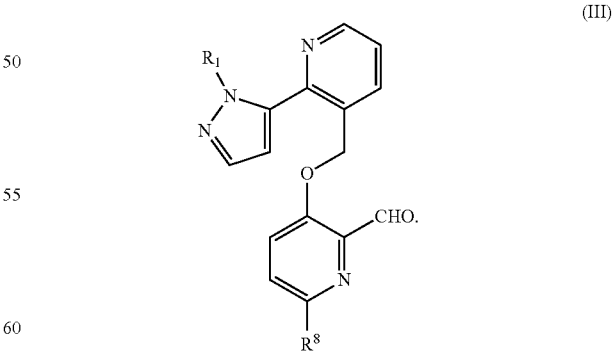

In some embodiments, $R^1$, for example, may be hydrogen. $R^1$ may be $C_1$-$C_6$ alkyl, such as methyl, ethyl, n-propyl, iso-propyl or butyl. $R^1$ may be $C_1$-$C_6$ alkyl substituted with 3-6 fluoro atoms, such as —$CH_2CHF_2$, —$CH_2CF_3$, or —$CH_2CH_2CF_3$. $R^1$ may be —$CO_2R^{2a}$, such as —$CH_2CO_2H$.

$R^2$ may be hydrogen. Alternatively, $R^2$ may be $C_1$-$C_6$ alkyl such as methyl, ethyl, n-propyl, iso-propyl or butyl.

In some embodiments, $R^8$ is hydrogen. In some embodiments, $R^8$ is $C_1$-$C_6$ alkyl such as methyl, ethyl, n-propyl, iso-propyl or butyl. In some embodiments, $R^8$ is OH. In some embodiments, $R^8$ is O—$C_1$-$C_6$ alkyl such as $OCH_3$, $OCH_2CH_3$, $OCH_2CH_2CH_3$, $OCHCH_3CH_3$ or O-butyl, optionally substituted with a 5- to 6-membered heterocycle containing at least 1 oxygen and/or nitrogen moiety. In some preferred embodiments, $R^8$ is $OCH_3$.

In other embodiments of the 1:1 adduct, the compound of formula (I) is of formula (IV):

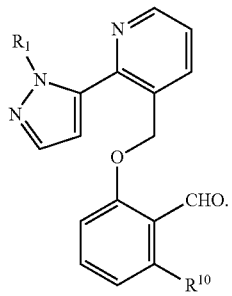

(IV)

In some embodiments, $R^1$, for example, may be hydrogen. $R^1$ may be $C_1$-$C_6$ alkyl, such as methyl, ethyl, n-propyl, iso-propyl or butyl. $R^1$ may be $C_1$-$C_6$ alkyl substituted with 3-6 fluoro atoms, such as —$CH_2CHF_2$, —$CH_2CF_3$, or —$CH_2CH_2CF_3$. $R^1$ may be —$CO_2R^{2a}$, such as —$CH_2CO_2H$. $R^2$ may be hydrogen. Alternatively, $R^2$ may be $C_1$-$C_6$ alkyl such as methyl, ethyl, n-propyl, iso-propyl or butyl.

In some embodiments, $R^{10}$ is hydrogen. In some embodiments, $R^{10}$ is $C_1$-$C_6$ alkyl such as methyl, ethyl, n-propyl, iso-propyl or butyl. In some preferred embodiments, $R^{10}$ is OH. In some embodiments, $R^8$ is O—$C_1$-$C_6$ alkyl such as $OCH_3$, $OCH_2CH_3$, $OCH_2CH_2CH_3$, $OCHCH_3CH_3$ or O-butyl, optionally substituted. In some preferred embodiments, $R^{10}$ is $OCH_3$.

In other embodiments of the 1:1 adduct, the compound of formula (I) is selected from the group in Table 1 consisting of:

TABLE 1

| | |
|---|---|
| 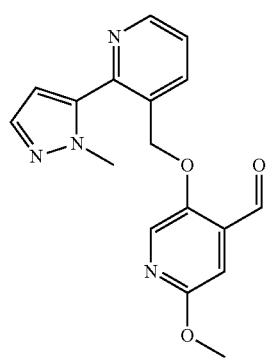 [SMILES: COc1cc(C=O)c(OCc2cccnc2-c2ccnn2C)cn1] | 1 |
| 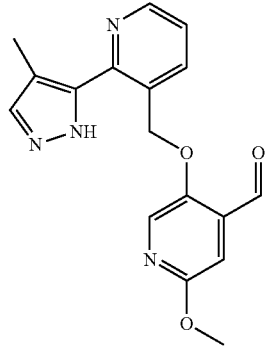 [SMILES: COc1cc(C=O)c(OCc2cccnc2-c2[nH]ncc2C)cn1] | 2 |
| 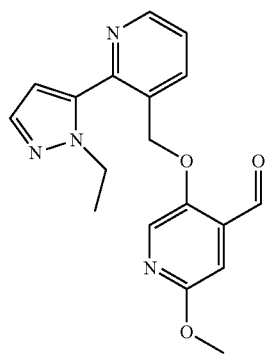 [SMILES: CCn1nccc1-c1ncccc1COc1cnc(OC)cc1C=O] | 3 |
| 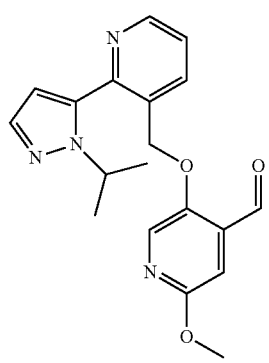 [SMILES: COc1cc(C=O)c(OCc2cccnc2-c2ccnn2C(C)C)cn1] | 4 |
| 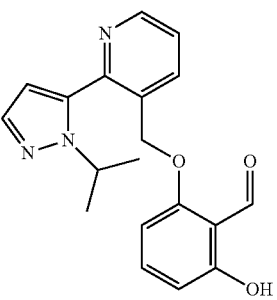 [SMILES: CC(C)n1nccc1-c1ncccc1COc1cccc(O)c1C=O] | 5 |

TABLE 1-continued
| | |
|---|---|
| 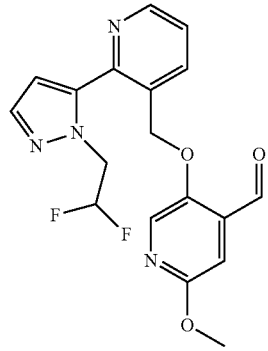 [SMILES: COc1cc(C=O)c(OCc2cccnc2-c2ccnn2CC(F)F)cn1] | 6 |
| 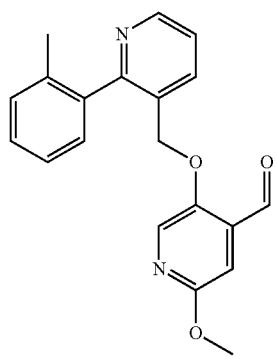 [SMILES: COc1cc(C=O)c(OCc2cccnc2-c2ccccc2C)cn1] | 7 |
| 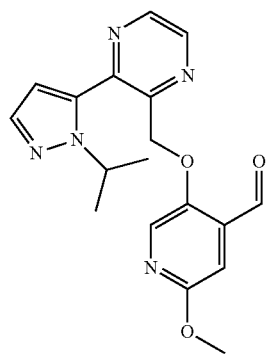 [SMILES: COc1cc(C=O)c(OCc2nccnc2-c2ccnn2C(C)C)cn1] | 8 |
| 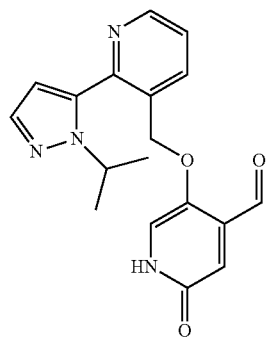 [SMILES: CC(C)n1nccc1-c1ncccc1COc1c[nH]c(=O)cc1C=O] | 9 |
TABLE 1-continued
| | |
|---|---|
| 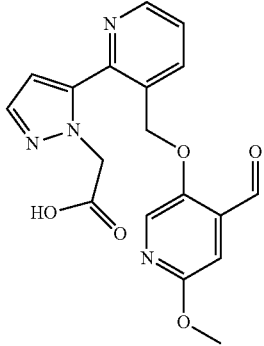 [SMILES: COc1cc(C=O)c(OCc2cccnc2-c2ccnn2CC(=O)O)cn1] | 10 |
| 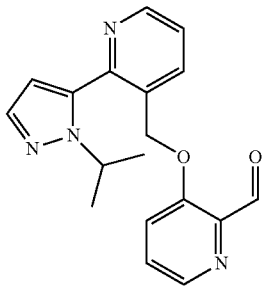 [SMILES: CC(C)n1nccc1-c1ncccc1COc1cccnc1C=O] | 11 |
| 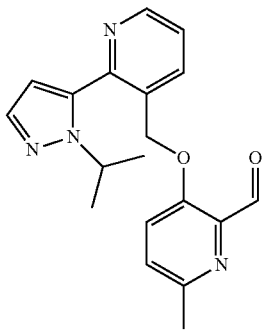 [SMILES: Cc1ccc(OCc2cccnc2-c2ccnn2C(C)C)c(C=O)n1] | 12 |
| 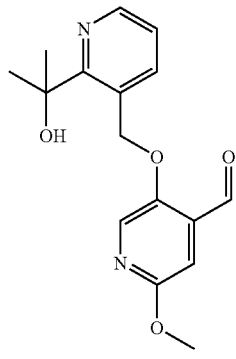 [SMILES: COc1cc(C=O)c(OCc2cccnc2C(C)(C)O)cn1] | 13 |

TABLE 1-continued
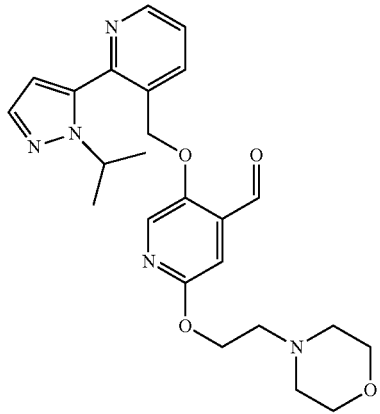 [SMILES: CC(C)n1nccc1-c1ncccc1COc1cnc(OCCN2CCOCC2)cc1C=O]
14
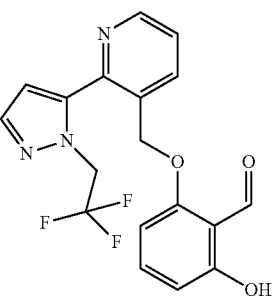 [SMILES: O=Cc1c(O)cccc1OCc1cccnc1-c1ccnn1CC(F)(F)F]
15
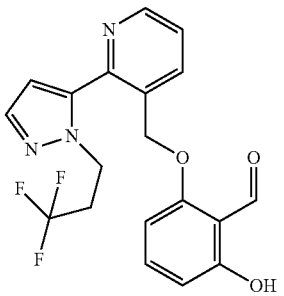 [SMILES: O=Cc1c(O)cccc1OCc1cccnc1-c1ccnn1CCC(F)(F)F]
16
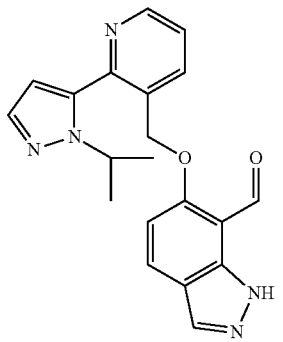 [SMILES: CC(C)n1nccc1-c1ncccc1COc1ccc2cn[nH]c2c1C=O]
17
TABLE 1-continued
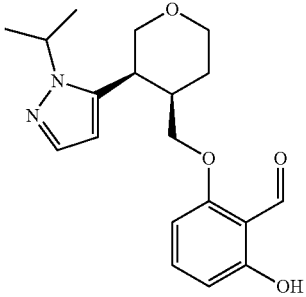 [SMILES: CC(C)n1nccc1[C@H]1COCC[C@H]1COc1cccc(O)c1C=O]
18
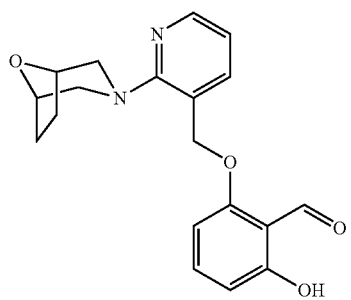 [SMILES: O=Cc1c(O)cccc1OCc1cccnc1N1CC2CCC(C1)O2]
19
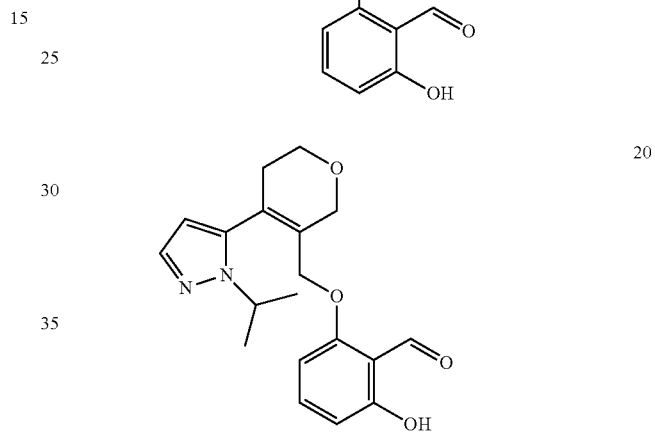
20
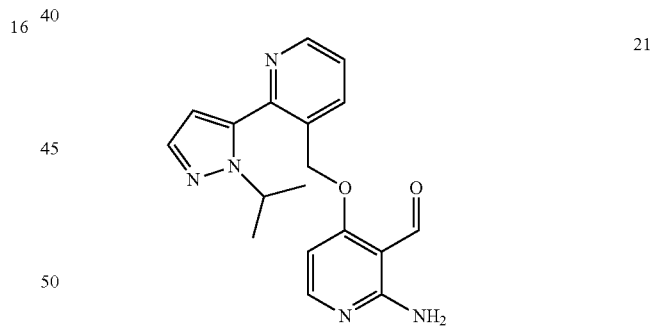
21
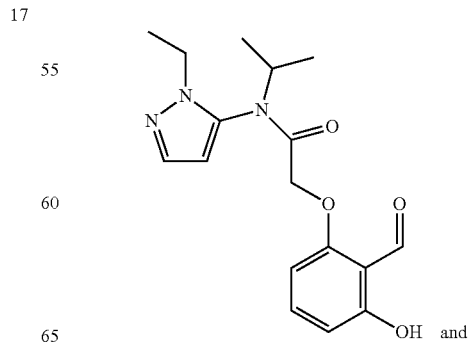
22
and TABLE 1-continued

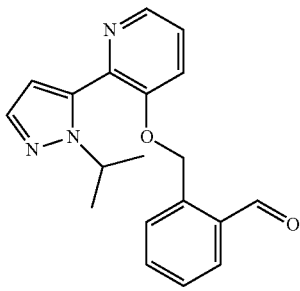 [SMILES: CC(C)n1nccc1-c1ncccc1OCc1ccccc1C=O]

or a pharmaceutically acceptable salt of each thereof.

In a preferred embodiment of the 1:1 adduct, the compound of formula (I) is

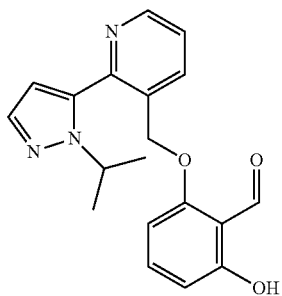 [SMILES: CC(C)n1nccc1-c1ncccc1COc1cccc(O)c1C=O]

or a pharmaceutically acceptable salt thereof.

In some embodiments, any of the 1:1 adducts described herein is formed in a subject in vivo and isolated from the subject.

Pharmaceutical Compositions

In further aspects of the invention, a 1:1 adduct of sickle hemoglobin (HbS) and a compound of formula (I) is provided by administering the compound of formula (I) to a subject. In some embodiments, the compound of formula (I) is provided to the subject as a pharmaceutical composition comprising any of the compounds described herein, and at least a pharmaceutically acceptable excipient.

Such pharmaceutical compositions can be formulated for different routes of administration. Although compositions suitable for oral delivery will probably be used most frequently, other routes that may be used include transdermal, intravenous, intraarterial, pulmonary, rectal, nasal, vaginal, lingual, intramuscular, intraperitoneal, intracutaneous, intracranial, and subcutaneous routes. Suitable dosage forms for administering any of the compounds described herein include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16$^{th}$ ed., A. Oslo editor, Easton Pa. 1980).

Pharmaceutically acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

The pharmaceutical compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. In certain embodiments, the compositions provided herein comprises one or more of α-tocopherol, gum arabic, and/or hydroxypropyl cellulose.

The compounds and pharmaceutical compositions described herein may be used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

Methods of Treatment

In further aspects of the invention, a method is provided for dosing a subject with a compound of formula (I), comprising administering an effective dosage of the compound of formula (I), wherein the effective dosage is predicated on the formation of a 1:1 adduct between the compound of formula (I) and sickle hemoglobin (HbS) in the subject, rather than being predicated on the formation of a 2:1 adduct between the compound of formula (I) and HbS in the subject. Accordingly, the method for dosing a subject based on the formation of the 1:1 adduct is safer than methods for dosing based on of the 2:1 adduct.

In further aspects of the invention, a method is provided of forming a 1:1 adduct of sickle hemoglobin (HbS) and a compound of formula (I), as claimed in any one of claims 1-5, comprising contacting the HbS with the compound of formula (I).

In still further aspects of the invention, a method is provided for increasing oxygen affinity of sickle hemoglobin (HbS) comprising contacting the HbS with a compound of formula (I), as claimed in any one of claims 1-5, to convert at a part to substantially all of the HbS to form a 1:1 adduct with the compound of formula (I).

Synthetic Methods

The reactions are preferably carried out in a suitable inert solvent that will be apparent to the skilled artisan upon reading this disclosure, for a sufficient period of time to ensure substantial completion of the reaction as observed by thin layer chromatography, $^1$H-NMR, etc. If needed to speed up the reaction, the reaction mixture can be heated, as is well known to the skilled artisan. The final and the intermediate compounds are purified, if necessary, by various art known methods such as crystallization, precipitation, column chromatography, and the likes, as will be apparent to the skilled artisan upon reading this disclosure.

An illustrative and non-limiting method for synthesizing a compound of formula (I), is schematically shown below. In the Schemes below as well as throughout the application, the following abbreviations have the following meanings. If not defined, the terms have their generally accepted meanings ° C.=degrees Celsius
RT=Room temperature
min=minute(s)
h=hour(s)
μL=Microliter
mL=Milliliter
mmol=Millimole
eq=Equivalent
mg=Milligram
ppm=Parts per million
LC-MS=Liquid chromatography-mass spectrometry
HPLC=High performance liquid chromatography
NMR=Nuclear magnetic resonance
Ph$_3$PBr$_2$=Triphenylphosphine dibromide
DMF=N, N-Dimethylformamide
DCM=Dichloromethane
THF=Tetrahydrofuran
DIAD=Diisopropyl azodicarboxylate
DEAD=Diethyl azodicarboxylate In the following Schemes, "A" refers to substituent "A" as described herein. ⊙ refers aryl, heteroaryl, heterocyclic or acyclic members of substituent "A" as described herein. ⊙ and ⊙ refer to rings B and C as described herein.

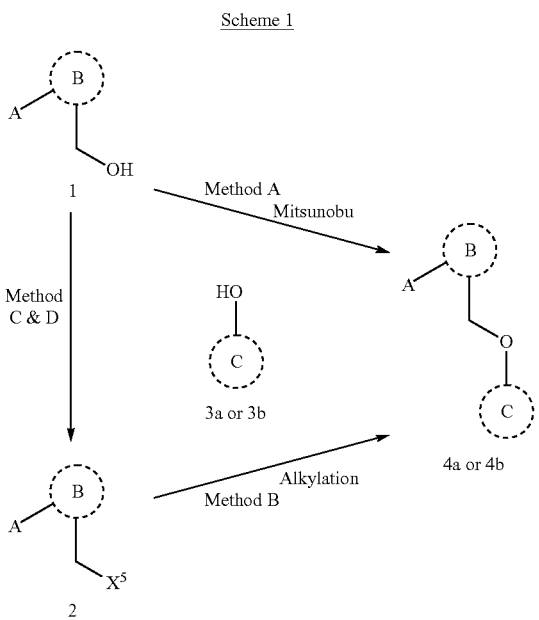

Scheme 1

General Method A (Scheme 1) for Preparing Analogs (4a/4b) from Substituted Methylene Alcohol (1) and Hydroxyl (Hetero)Aryl Aldehyde Derivatives (3a/3b).

A hydroxyl (hetero)arylaldehyde derivatives (3a/3b) (0.1-2 mmol) mixture with substituted methylene alcohol (1) (0.8 to 1.2 eq) and PPh$_3$ (1-1.5 eq) in anhydrous THF (1-10 mL) was stirred under nitrogen until complete dissolution. The solution was cooled to 0° C. on ice bath and DIAD or DEAD (1.1 eq) in THF or toluene was added dropwise over a 1-20 min period. The ice cooling bath was allowed to expire over 90 min and the mixture was stirred at RT for 2-48 hours. The mixture was stirred for 10 min, then filtered through a pad of silica. The silica was washed with ethyl acetate 2-20 mL. The combined filtrates were evaporated and the residue was dried on highvac. The residue was purified by preparative HPLC or flash silica gel chromatography.

General Method B (Scheme 1) for Preparing Analogs (4a/4b) from Substituted Methylene Halide (2) and Hydroxyl (Hetero)Aryl Aldehyde Derivatives (3a/3b).

A mixture of hydroxyl (hetero)arylaldehyde derivatives (3a/3b) (0.1-2 mmol, 1-4 eq.), substituted methylene chloride or bromide (2) (1 eq), and K$_2$CO$_3$ (2-5 eq.) (catalytic amount of NaI or Bu$_4$NI may also be added) in DMF or acetonitrile (1 to 10 mL) was stirred at RT or heating up to 120° C. for 0.5-8 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous NH$_4$Cl was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvents mixture (e.g., ethyl acetate/hexanes).

General Method C (Scheme 1) for Preparing Substituted Methylene Chloride (2a).

To a solution of substituted methylene alcohol (1) (0.1 to 2 mmol) in DCM (1-10 mL) was added SOCl$_2$ dropwise (2 eq to 5 eq) at 0° C. or RT. The reaction mixture was stirred at RT for 10 min to 6 h, or until reaction is judged complete (LC/MS). The reaction mixture is concentrated to dryness over a rotavap. The crude chloride residue was suspended in toluene, sonicated and concentrated to dryness. The process was repeated three times and dried under vacuum to give the substituted methylene chloride (2), usually as an off-white solid, which was used for next step without further purification. Alternatively, a solution of aqueous 1N Na$_2$CO$_3$ is then added to produce a solution of pH~8. the mixture was extracted with DCM (3×10-50 mL), dried over sodium sulfate, and concentrated to the crude substituted methylene chloride (2a), which is then purified by column chromatography on silica gel (0-100% ethyl acetate-hexanes).

General Method D (Scheme 1) for Preparing Substituted Methylene Bromide (2b).

To a solution of substituted methylene alcohol (1) (0.1 to 2 mmol) in DCM (1-10 mL) was added Ph$_3$PBr$_2$ dropwise (2 eq to 5 eq) at 0° C. or RT. The reaction mixture was stirred at RT for 10 min to 2 h, or until reaction is judged complete (LC/MS). The reaction mixture is concentrated to dryness over a rotavap. The residue purified by column chromatography on silica gel (0-100% ethyl acetate-hexanes) to afford the pure bromide 2b.

Methods for making some of the compounds summarized herein (e.g., compounds 1-8, 10-13, 15 and 16 of Table 1) are provided in the published applications US 2013/0190315 and US 2013/0190316, both of which are incorporated herein in their entireties. Methods for making the remaining compounds in Table 1 (e.g., compounds 9, 14 and 17-23) are described below.

Example 1
Preparation of 2-oxo-5-[[2-(2-propan-2-ylpyrazol-3-yl)pyridin-3-yl]methoxy]-1H-pyridine-4-carbaldehyde (compound 9 in Table 1)
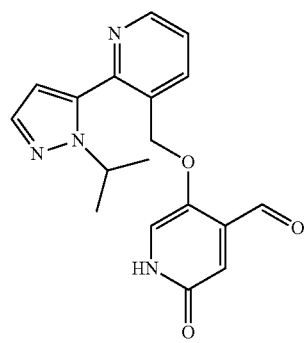
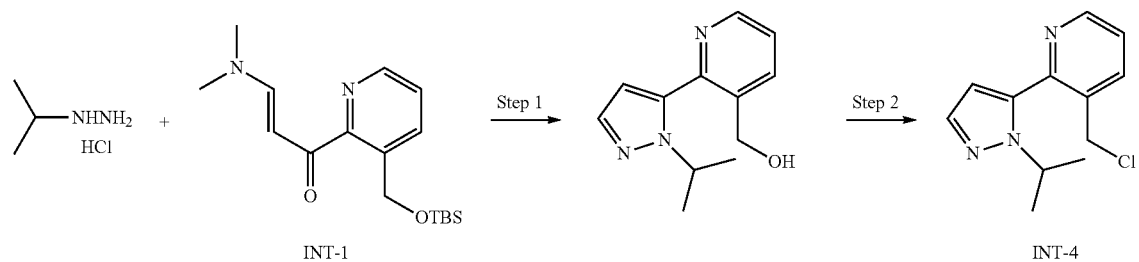
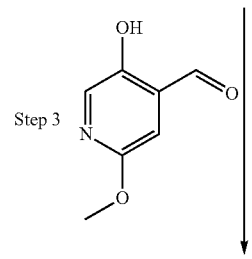
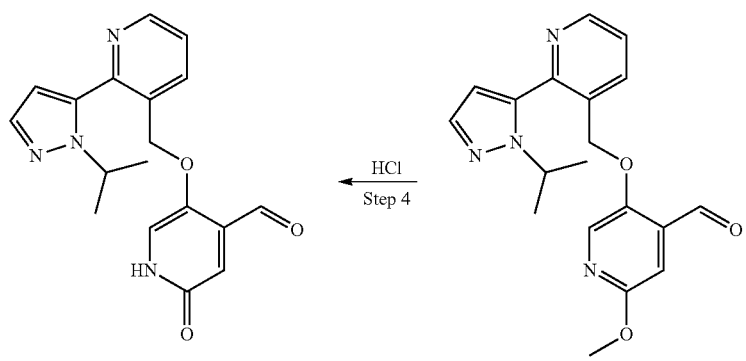

Step 1:

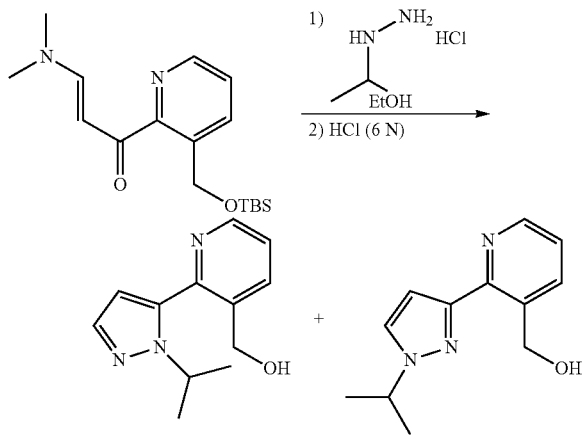

To (E)-1-(3-((tert-butyldimethylsilyloxy)methyl)pyridin-2-yl)-3-(dimethylamino)prop-2-en-1-one (crude, 1.03 g, 3.22 mmol, 1 eq.; INT-1) in EtOH (10 mL) was added isopropylhydrazine hydrochloride (430 mg, 3.86 mmol, 1.2 eq.). The mixture was heated at 80° C. for 2 h, cooled, added HCl (6 N, 0.5 mL), and stirred O/N. The mixture was concentrated and diluted with EtOAc (80 mL) and NaHCO$_{3(sat)}$ (10 mL) solution. The layers were separated and the aqueous layer was extracted with EtOAc three times. The combined organic layers were dried over Na$_2$SO$_4$, concentrated, and purified on silica gel using EtOAc as eluent to give (2-(1-isopropyl-1H-pyrazol-5-yl)pyridin-3-yl)methanol (500 mg, 71%) and (2-(1-isopropyl-1H-pyrazol-3-yl)pyridin-5-yl)methanol (55 mg, 25%) as pale yellow oils. Data for 2-(1-isopropyl-1H-pyrazol-5-yl)pyridin-3-yl)methanol: $^1$H NMR (400 MHz, CDCl$_3$) δ 8.67 (dd, J=4.7, 1.5 Hz, 1H), 8.0 (d, J=7.8 Hz, 1H), 7.61 (d, J=1.8 Hz, 1H), 7.39 (dd, J=7.8, 4.8 Hz, 1H), 6.37 (d, J=1.8 Hz, 1H), 4.67 (s, 2H), 4.55 (sep, J=6.6 Hz 1H), 1.98-2.05 (br, 1H), 1.47 (d, J=6.6 Hz, 6H). LRMS (M+H$^+$) m/z 218.1 Data for (2-(1-isopropyl-1H-pyrazol-3-yl)pyridin-5-yl)methanol: $^1$H NMR (400 MHz, CDCl$_3$) δ 8.62 (dd, J=4.8, 1.6 Hz, 1H), 7.72 (d, J=7.6 Hz, 1H), 7.55 (d, J=2.4 Hz, 1H), 7.23 (dd, J=7.6, 4.8 Hz, 1H), 6.99 (dd, J=8.0, 6.5 Hz, 1H), 6.07 (t, J=7.6 Hz, 1H), 4.67 (d, J=7.6 Hz, 2H), 4.58 (sep, J=6.7 Hz, 1H), 1.60 (d, J=6.7 Hz, 1H). MS (ESI) m/z 218.1 [M+H]$^+$.

Step 2:

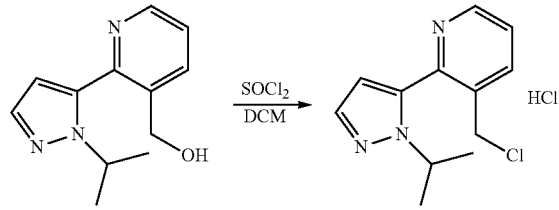

To (2-(1-isopropyl-1H-pyrazol-5-yl)pyridin-3-yl)methanol (560 mg, 2.58 mmol) in DCM (10 mL) was added SOCl$_2$ (3.0 mL) at RT. The reaction mixture was stirred at RT for 4 h and concentrated to dryness. The crude solid was suspended in toluene and concentrated to dryness. The process was repeated three times and dried under vacuum to give 3-(chloromethyl)-2-(1-isopropyl-1H-pyrazol-5-yl)pyridine hydrochloride (700 mg) as an off-white solid, which was used for next step without further purification.

Step 3:

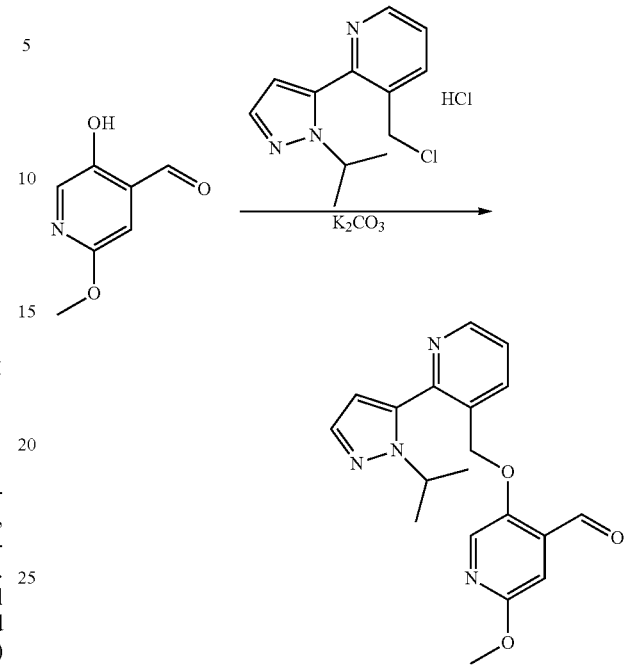

A mixture of 5-hydroxy-2-methoxyisonicotinaldehyde (395 mg, 2.58 mmol, 1 eq.), 3-(chloromethyl)-2-(1-isopropyl-1H-pyrazol-5-yl)pyridine hydrochloride (700 mg, 2.58 mmol, 1 eq.), and K$_2$CO$_3$ (1.4 g, 10.32 mmol, 4 eq.) in DMF (10.0 mL) was heated at 70° C. for 2 h. The mixture was cooled, filtered, concentrated, and purified on silica gel using a mixture of EtOAc and hexanes as eluent to give 5-((2-(1-isopropyl-1H-pyrazol-5-yl)pyridin-3-yl)methoxy)-2-methoxyisonicotinaldehyde (590 mg, 65%) as an off-white solid. $^1$H NMR (400 MHz, CDCl$_3$) δ 10.41 (s, 1H), 8.76 (dd, J=4.7, 1.6 Hz, 1H), 8.04 (dd, J=7.9, 1.6 Hz, 1H), 7.90 (s, 1H), 7.61 (d, J=1.8 Hz, 1H), 7.44 (dd, J=7.9, 4.8 Hz, 1H), 7.10 (s, 1H), 6.37 (d, J=1.8 Hz, 1H), 5.14 (s, 2H), 4.65 (sep, J=6.6 Hz, 1H), 3.91 (s, 3H), 1.49 (d, J=6.6 Hz, 6H); MS (ESI) m/z 353.1 [M+H]$^+$.

To 5-((2-(1-isopropyl-1H-pyrazol-5-yl)pyridin-3-yl)methoxy)-2-methoxyisonicotinaldehyde (590 mg) suspended in water (5.0 mL) was added HCl (6 N, 4 mL). Once the mixture turned into a homogeneous solution, it was freeze at −78° C. to an solid and pump under high vacuum O/N. The yellow solid was continued to pump at 45° C. for 20 h, dissolved in water (2.0 mL), and basified to pH 11 with NaOH (2 N). The aqueous layer was washed with DCM three times and the pH of the mixture was adjusted to pH 6-7. The solid was collected and dried to give 2-oxo-5-[[2-(2-propan-2-ylpyrazol-3-yl)pyridin-3-yl]methoxy]-1H-pyridine-4-carbaldehyde as a yellow solid. $^1$H NMR (400 MHz, CDCl$_3$) δ 10.3 (s, 1H), 8.8 (dd, J=4.7, 1.6 Hz, 1H), 8.1 (dd, J=7.9, 1.5 Hz, 1H), 7.6 (s, 1H), 7.5 (d, J=1.8 Hz, 1H), 7.1 (s, 1H), 7.0 (s, 1H), 6.6 (d, J=1.8 Hz, 1H), 4.9 (s, 2H), 4.7 (sep, J=6.6 Hz, 1H), 1.5 (d, J=6.6 Hz, 6H); MS (ESI) m/z 339.4 [M+H]$^+$.

Example 2

Preparation of 2-(2-morpholin-4-ylethoxy)-5-[[2-(2-propan-2-ylpyrazol-3-yl)pyridin-3-yl]methoxy]pyridine-4-carbaldehyde (compound 14 in Table 1)

according to general method B, from 5-hydroxy-2-(2-morpholinoethoxyl)isonicotinaldehyde and INT-4.

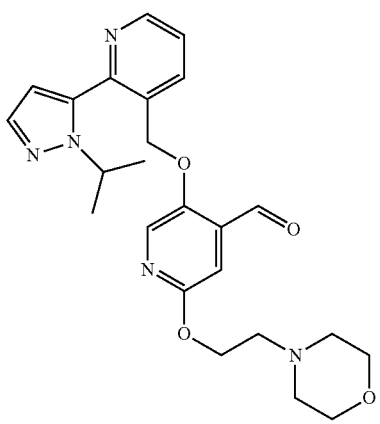 [SMILES: CC(C)n1nccc1-c1ncccc1COc1cnc(OCCN2CCOCC2)cc1C=O]

$^1$H NMR (400 MHz, Chloroform-d) δ 10.33 (s, 1H), 8.68 (dd, J=4.8, 1.7 Hz, 1H), 7.95 (dd, J=7.9, 1.7 Hz, 1H), 7.79 (s, 1H), 7.53 (d, J=1.8 Hz, 1H), 7.36 (dd, J=7.9, 4.7 Hz, 1H), 7.04 (s, 1H), 6.28 (d, J=1.8 Hz, 1H), 5.06 (s, 2H), 4.57 (s, OH), 4.32 (t, J=5.7 Hz, 2H), 3.69-3.62 (m, 4H), 2.70 (t, J=5.7 Hz, 2H), 2.53-2.45 (m, 4H), 1.41 (d, J=6.6 Hz, 6H); MS (ESI) m/z 452 [M+H]$^+$.

Preparation of 3-(chloromethyl)-2-(1-isopropyl-1H-pyrazol-5-yl)pyridine (INT-4)

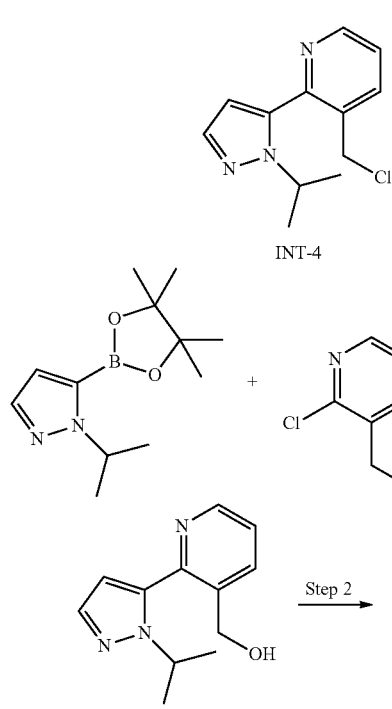

Step 1.

To a 500-mL flask containing the pyrazole boronate (9.0 g, 38.1 mmol), 2-chloropyridine (5.47 g, 38.1 mmol), Pd(dppf)Cl$_2$ ([1,1-bis(diphenylphosphino)ferrocene]dichloropalladium) (1.39 g, 1.91 mmol, 5% mol), and sodium bicarbonate (9.61 g, 114.4 mmol, 3 equiv) was added 100 mL of dioxane and 30 mL of water. The mixture was heated under nitrogen at 100° C. for 12 hrs. Then solvents were removed on a rotavap at 40° C. undervacum. The resulting brown residue was suspended in 20% EtOAc/DCM (60 mL), filtered through a pad of silica gel (15 g); washed with 20% EtOAc/DCM (4×20 mL). The combined filtrate were concentrated to afford a brown oil (13 g). The residue was dissolved 10% EtOAc/hexanes (20 mL) and loaded on a Biotage 100 g snap SiO2 column and eluted with 0-50% EtOAc. (2-(1-isopropyl-1H-pyrazol-5-yl)pyridin-3-yl)methanol was obtained as a light brown oil (3.32 g, 40%). MS (ESI) m/z 218 [M+H]$^+$.

Step 2.

To a solution of (2-(1-isopropyl-1H-pyrazol-5-yl)pyridin-3-yl)methanol) (440 mg, 2.02 mmol) in DCM (4 mL) was added SOCl$_2$ (2 eq) at 0° C. The reaction mixture was stirred at RT for 15 mins and concentrated to dryness. The crude solid was suspended in toluene and concentrated to dryness. The process was repeated three times and dried under vacuum to give 3-(chloromethyl)-2-(1-isopropyl-1H-pyrazol-5-yl)pyridine hydrochloride (432 mg) as an off-white solid, which was used for next step without further purification. MS (ESI) m/z 236.5 [M+H]$^+$.

Example 3

Preparation of 6-((2-(1-isopropyl-1H-pyrazol-5-yl)pyridin-3-yl)methoxy)-1H-indazole-7-carbaldehyde (compound 17 in Table 1)

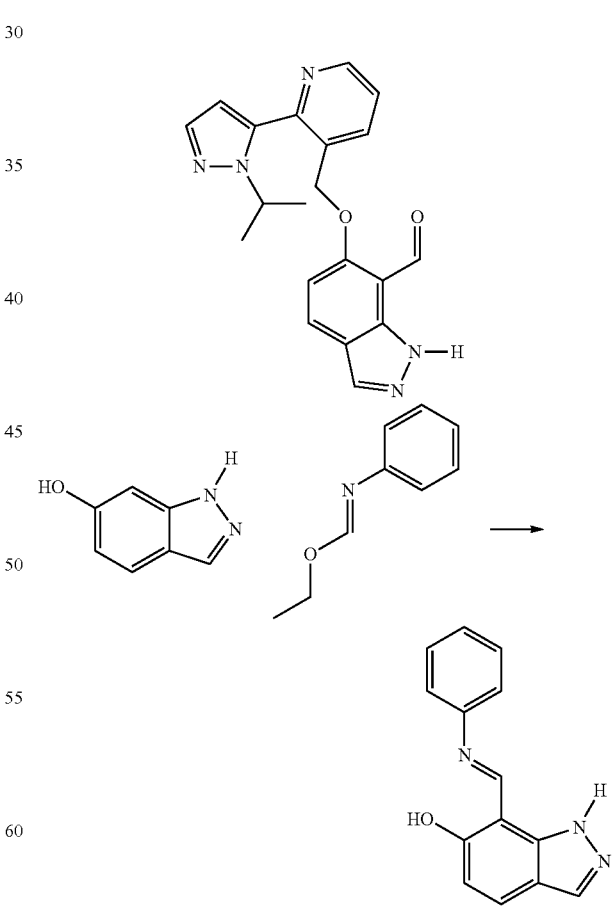

To a flask equipped with a Vigreux-style column was added 1H-indazol-6-ol (0.5 g, 3.73 mmol, 1 eq.) and ethyl N-phenylformimidate (1.11 g, 7.46 mmol, 2 eq.) The reaction mixture was heated to 175° C. in a heat block for 2 h and then cooled and carried directly into the next step.

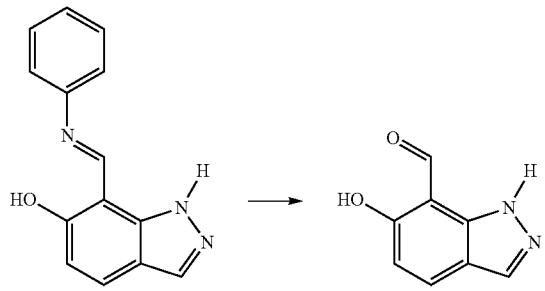 [SMILES: Oc1ccc2cn[nH]c2c1/C=N/c1ccccc1 ; O=Cc1c(O)ccc2cn[nH]c12]

7-((Phenylimino)methyl)-1H-indazol-6-ol (~1.8 g, 7.46 mmol) was suspended in 5M aqueous HCl (25 ml) and stirred in a 50° C. heat block for 4 h. The reaction solution was allowed to cool and then extracted with ethyl acetate (4×50 ml). The pH of the aqueous phase was adjusted to ~4 by addition of an aqueous saturated sodium bicarbonate solution and extracted with ethyl acetate (1×50 ml). The pH of the aqueous phase was adjusted again to ~8 with sodium bicarbonate solution and extracted with ethyl acetate (1×50 ml). The combined organic phases were washed with an aqueous 10% citric acid solution (80 ml), water (50 ml) and an aqueous saturated sodium chloride solution (50 ml). The extractions were then dried over sodium sulfate, concentrated and purified by silica gel chromatography (10-100% ethyl acetate/ hexanes) to give 6-hydroxy-1H-indazole-7-carbaldehyde (0.4 g, 33%) as an orange solid. $^1$H NMR (400 MHz, CDCl$_3$) δ 10.44 (s, 1H), 8.03 (s, 1H), 7.85 (d, J=8.8 Hz, 1H), 6.80 (d, J=8.8 Hz, 1H). MS (ESI) m/z 163 [M+H]$^+$.

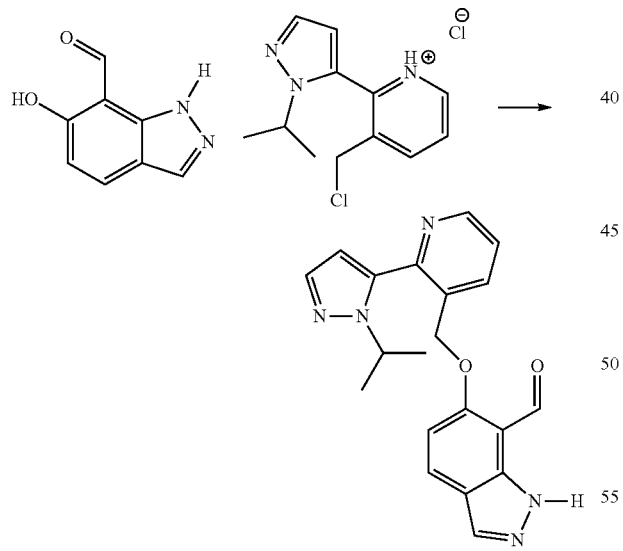

6-Hydroxy-1H-indazole-7-carbaldehyde (0.14 g, 0.86 mmol, 1 eq.) was dissolved in N,N-dimethylformamide (4 ml). 3-(Chloromethyl)-2-(1-isopropyl-1H-pyrazol-5-yl)pyridin-1-ium chloride (0.235 g, 0.86 mmol, 1 eq.) and potassium carbonate (0.36 g, 2.6 mmol, 3 eq.) were added and the reaction mixture was stirred in a 50° C. heat block for 16 h. The reaction mixture was then cooled, and ethyl acetate (100 ml) and water (50 ml) were added. The phases were separated and the aqueous phase was extracted with more ethyl acetate (2×50 ml). The combined organic phases were washed with water (50 ml) and aqueous saturated sodium chloride solution (50 ml), and dried over sodium sulfate. After concentration the residue was purified by silica gel chromatography (5-70% ethyl acetate/hexanes). Product fractions were triturated with diethyl ether and lyophilized from acetonitrile/water to give 6-((2-(1-isopropyl-1H-pyrazol-5-yl)pyridin-3-yl)methoxy)-1H-indazole-7-carbaldehyde (0.16 g, 51%) as an off-white solid. $^1$H NMR (400 MHz, CDCl$_3$) δ 11.59 (s, 1H), 10.58 (s, 1H), 8.74 (dd, J=4.4, 1.6 Hz, 1H), 8.02 (d, J=1.6 Hz, 1H), 8.01 (s, 1H), 7.90 (d, J=8.8 Hz, 1H), 7.58 (d, J=1.8 Hz, 1H), 7.42 (dd, J=7.9, 4.8 Hz, 1H), 6.75 (d, J=8.8 Hz, 1H), 6.36 (d, J=1.8 Hz, 1H), 5.22 (s, 2H), 4.66 (septet, J=6.6 Hz, 1H), 1.46 (d, J=6.6 Hz, 6H). MS (ESI) m/z 362 [M+H]$^+$.

Example 4

Preparation of 2-hydroxy-6-[[cis-3-(2-propan-2-ylpyrazol-3-yl)oxan-4-yl]methoxy]benzaldehyde (compound 18 in Table 1)

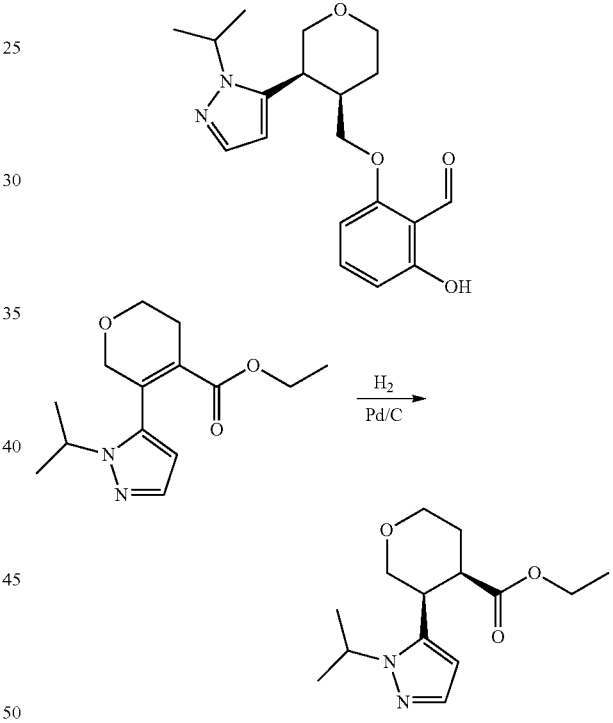

Step 1:

To a solution of ethyl 5-(1-isopropyl-1H-pyrazol-5-yl)-3,6-dihydro-2H-pyran-4-carboxylate (100 mg, 0.38 mmol) in EtOH (2 mL) was added Pd/C (50 mg), then it was charged with H$_2$ (1 atm) and stirred at room temperature for 3 days, Mass spec shows about 50% conversion. The mixture was then added a solution of NH$_4$CO$_2$H (200 mg) in water (2 ml) and additional Pd/C, and the mixture was further heated at 75° C. for 1.5 h, after cooled to room temperature, the reaction was diluted with EtOH, pd/C was filtered off, and the filtrate was concentrated to give crude oil, which was diluted with CHCl3, organic layer was washed with Sat. NaHCO$_3$, dried and concentrated to give crude product, which was purified by column (Hexanes/EtOAc=65:35) to give (±)ethyl(3S,4R)-3-(1-isopropyl-1H-pyrazol-5-yl)tetrahydro-2H-pyran-4-carboxylate (70 mg).

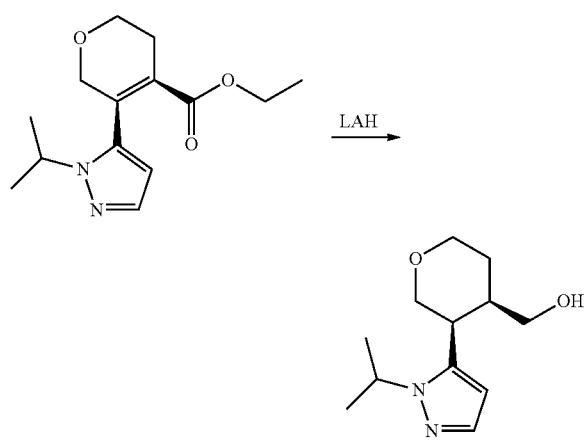

Step 2:

To a solution of (±)(3S,4R)-ethyl 3-(1-isopropyl-1H-pyrazol-5-yl)tetrahydro-2H-pyran-4-carboxylate (70 mg, 0.26 mmol) in THF (1.5 mL) at −15° C. was added 1M LiAH₄ solution in THF (0.34 mL, 0.34 mmol) slowly. After stirred for 30 min, it was quenched with Sat. NH₄Cl; the mixture was extracted with EtOAc. Organic layers were combined, dried and concentrated to give (±)(3S,4R)-3-(1-isopropyl-1H-pyrazol-5-yl)tetrahydro-2H-pyran-4-yl)methanol as crude product (60 mg).

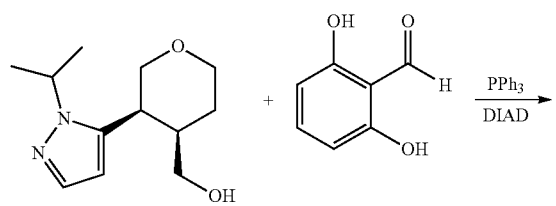

Step 3:

To a solution of (±)((3S,4R)-3-(1-isopropyl-1H-pyrazol-5-yl)tetrahydro-2H-pyran-4-yl)methanol (50 mg, 0.22 mmol) and 2,6-dihydroxybenzaldehyde (60 mg, 0.44 mmol) in THF (1 mL) was added PPh₃ (120 mg, 0.44 mmol) and DIAD (0.09 mL, 0.44 mmol) at 0° C. After stirred for 30 min, the solution was concentrated and the residue was purified by column (Hexanes/EtOAc=60:40) to give impure product, which was further purified by prep HPLC (eluted with ACN/H₂O) to give (±) 2-hydroxy-6-(((3S,4R)-3-(1-isopropyl-1H-pyrazol-5-yl)tetrahydro-2H-pyran-4-yl)methoxy)benzaldehyde (6 mg). 1H NMR (400 MHz, CDCl₃) (ppm) 11.90 (s, 1H), 10.36 (s, 1H), 7.79 (s, 1H), 7.50 (d, J=2.0 Hz, 1H), 7.32 (t, J=8.8 Hz, 1H), 6.52 (d, J=8.4 Hz, 1H), 6.43 (d, J=1.6 Hz, 1H), 6.16 (d, J=8.0 Hz, 1H), 4.46 (m, 1H), 4.13 (dt, J=11.2, 4.0 Hz, 1H), 3.95 (dd, J=11.2, 3.2 Hz, 1H), 3.81 (dd, J=11.6, 3.2 Hz, 1H), 3.73 (dd, J=9.2, 5.6 Hz, 1H), 3.65 (dt, J=11.6, 3.2 Hz, 1H), 3.57 (t, J=8.8 Hz, 1H), 3.28 (d, J=4.0 Hz, 1H), 2.56 (m, 1H), 1.87 (m, 1H), 1.58 (m, 1H), 1.31 (d, J=6.8 Hz, 3H), 1.29 (d, J=7.6 Hz, 3H); MS (ESI) m/z 334.3 [M+H]⁺.

Step 5:

To a solution of tert-butyl 4-(bromomethyl)-5-(1-isopropyl-1H-pyrazol-5-yl)-3,6-dihydropyridine-1(2H)-carboxylate (18 mg, 0.05 mmol) and

10 mg, 0.06 mmol) in DMF (1 mL) is added K₂CO₃ (14 mg, 0.1 mmol). After stirring at room temperature for 1 h, it is diluted with water and EtOAc, organic layer is separated, and the aqueous layer is extracted with EtOAc, organic layer is combined, washed with brine, dried and concentrated to give crude product, which is purified by column (Hexanes/EtOAc=2:1.

Example 5

Preparation of 2-((2-(8-oxa-3-azabicyclo[3.2.1]octan-3-yl)pyridin-3-yl)methoxy)-6-hydroxybenzaldehyde (compound 19 in Table 1)

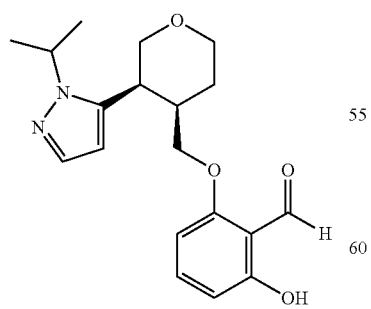
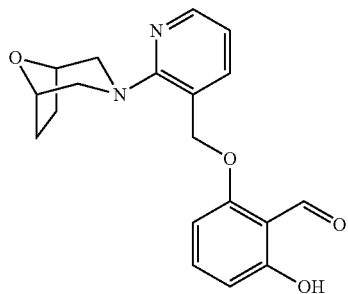 [SMILES: O=Cc1c(O)cccc1OCc1cccnc1N1CC2CCC(C1)O2]

The compound was prepared from ethyl 2-fluoronicotinate and 8-oxa-3-azabicyclo[3.2.1]octane according to reaction scheme below.

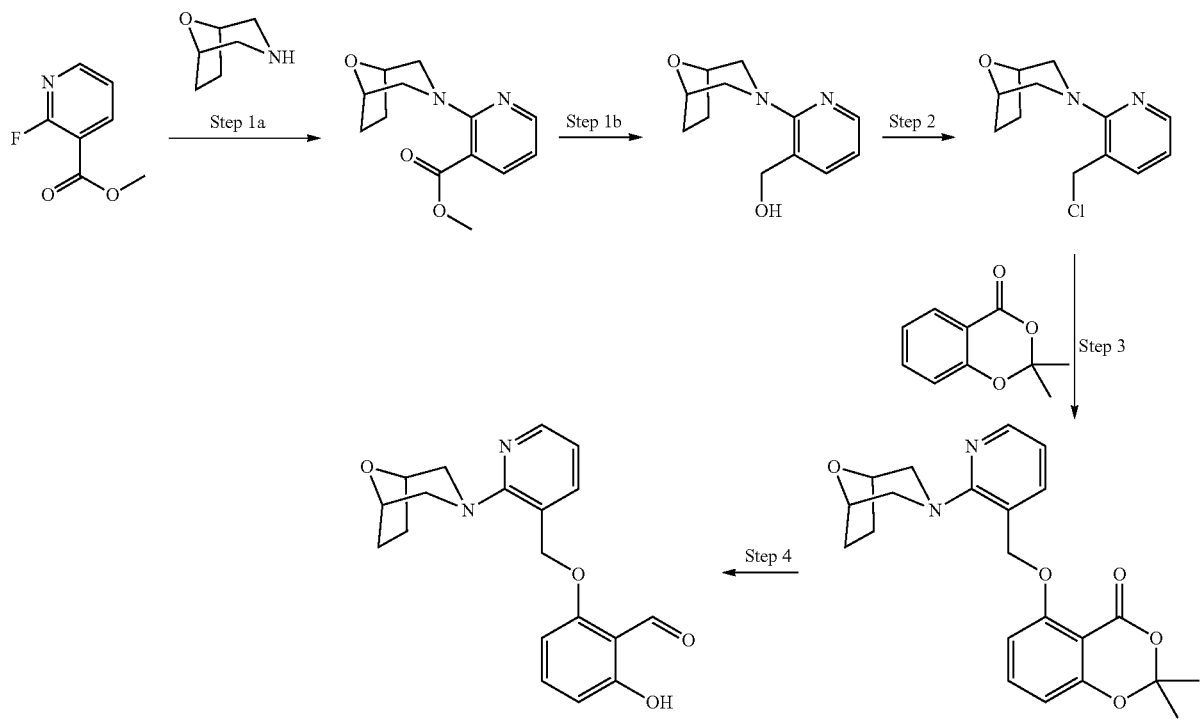

Step 1a.

To a solution of ethyl 2-fluoronicotinate (0.15 g, 0.97 mmol) in NMP (0.5 mL) was added diisopropylethyl amine (0.50 mL, 2.9 mmol), and 8-oxa-3-azabicyclo[3.2.1]octane (0.17 g, 0.72 mmol). The resulting mixture was irradiated with microwaves (100° C.) for 1 h and loaded directly onto a silica column. Eluting the column with EtOAc/hexanes (0-100%) provided methyl 2-(8-oxa-3-azabicyclo[3.2.1]octan-3-yl)nicotinate as a clear oil (0.100 g, 42% yield). MS (ES) for $C_{13}H_{16}N_2O_3$: 249 (MH$^+$).

Step 1b.

To a cooled (0° C.) solution of 2-(8-oxa-3-azabicyclo[3.2.1]octan-3-yl)nicotinate (0.10 g, 0.40 mmol) in THF (5 mL) was added a solution of lithium aluminum hydride (1.2 mL, 1M in THF). The reaction mixture was stirred for 1 h and then 20 μL of H$_2$O was added followed by 20 μL of 15% NaOH (aq) and then 60 μL of additional H$_2$O. The slurry was stirred for 1 h, filtered and the resulting residue was washed with ether. The combined organic layers were dried over MgSO$_4$ and concentrated in vacuo to yield (2-(8-oxa-3-azabicyclo[3.2.1]octan-3-yl)pyridin-3-yl)methanol (0.070 g, 79% yield). MS (ES) for $C_{12}H_{16}N_2O_2$: 221 (MH$^+$).

Step 2.

To a cooled (0° C.) solution of (2-(8-oxa-3-azabicyclo[3.2.1]octan-3-yl)pyridin-3-yl)methanol (0.070 g, 0.32 mmol) in dichloromethane was added SOCl$_2$ (0.23 mL, 3.2 mmol) and the reaction mixture was allowed to warm to ambient temperature. After 1 h, the reaction mixture was concentrated and azeotroped with toluene three times to provide 3-(3-(chloromethyl)pyridin-2-yl)-8-oxa-3-azabicyclo[3.2.1]octane (0.075 g, 98%) as a clear oil. MS (ES) for $C_{12}H_{15}ClN_2O$: 239 (MH$^+$).

Step 3.

To a solution of provide 3-(3-(chloromethyl)pyridin-2-yl)-8-oxa-3-azabicyclo[3.2.1]octane (0.080 g, 0.35 mmol) and 5-hydroxy-2,2-dimethyl-4H-benzo[d][1,3]dioxin-4-one (0.061 g, 0.31 mmol) in DMF was added cesium carbonate (0.307 g, 0.94 mmol) and the reaction mixture was heated (60° C.). After 30 minutes, the reaction mixture was partitioned between EtOAc and saturated aqueous sodium bicarbonate and the aqueous layer was extracted two times with EtOAc. Combined organic layers were washed with brine, dried over MGSO4 and concentrated in vacuo. Purification by silica gel chromatography yielded 5-((2-(8-oxa-3-azabicyclo[3.2.1]octan-3-yl)pyridin-3-yl)methoxy)-2,2-dimethyl-4H-benzo[d][1,3]dioxin-4-one (112 mg, 90% yield). MS (ES) for $C_{22}H_{24}N_2O_5$: 397 (MH$^+$).

Step 4.

To a cooled (−78° C.) solution of 5-((2-(3-oxa-8-azabicyclo[3.2.1]octan-8-yl)pyridin-3-yl)methoxy)-2,2-dimethyl-4H-benzo[d][1,3]dioxin-4-one (0.11 g, 0.28 mmol) in CH$_2$Cl$_2$ was added DIBAL-H (0.85 mL, 1M in CH$_2$Cl$_2$) and reaction mixture was allowed to warm to ambient temperature over 3 hours. The reaction mixture was then cooled (−78° C.) and MeOH was added followed by saturated potassium sodium tartrate solution (300 μL). This mixture was stirred for 2 hours at ambient temperature and filtered over Celite. The resulting solution was partitioned between EtOAc and saturated aqueous NaHCO$_3$ and washed two times with EtOAc. The combined organic layers were washed with brine, dried over MgSO$_4$ and concentrated in vacuo. Purification by preparatory HPLC resulted in 2-((2-(8-oxa-3-azabicyclo[3.2.1]octan-3-yl)pyridin-3-yl)methoxy)-6-hydroxybenzaldehyde (0.025 g, 25% yield). $^1$H NMR (400 MHz, Chloroform-d) δ 11.95 (s, 1H), 10.39 (d, J=0.6 Hz, 1H), 8.32 (dd, J=4.8, 1.9 Hz, 1H), 7.74 (dd, J=8.0, 2.1 Hz, 1H), 7.40 (t, J=8.4 Hz, 1H), 7.00 (dd, J=7.5, 4.8 Hz, 1H), 6.56 (d, J=8.5 Hz, 1H), 6.39 (d, J=8.3 Hz, 1H), 5.15 (s, 2H), 4.47-4.40 (m, 2H), 3.33 (dd, J=12.5, 2.0 Hz, 2H), 3.03 (dd, J=12.3, 1.4 Hz, 2H), 2.13-1.94 (m, 4H). MS (ES) for $C_{19}H_{20}N_2O_4$: 341 (MH$^+$).

Example 6

Preparation of 2-hydroxy-6-((5-(1-isopropyl-1H-pyrazol-5-yl)-3,6-dihydro-2H-pyran-4-yl)methoxy)benzaldehyde (compound 20 in Table 1)

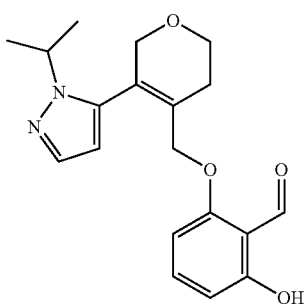

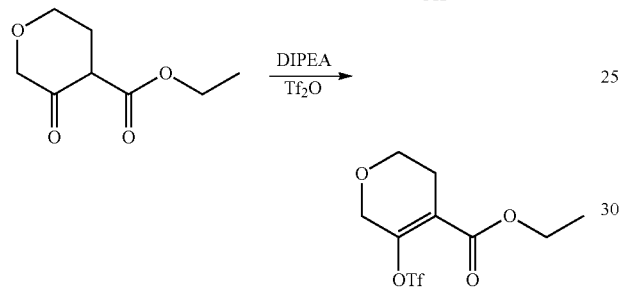

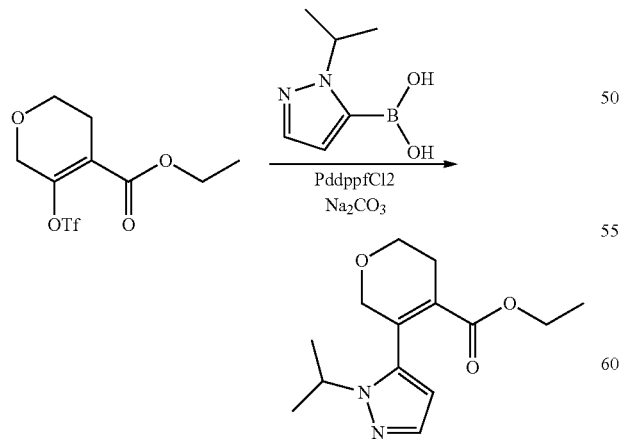

Step 1:

To a solution of ethyl 3-oxotetrahydro-2H-pyran-4-carboxylate (1.0 g, 5.81 mmol) in DCM (30 mL) was added DIPEA (1.22 mL, 6.97 mmol) and Tf$_2$O (1.08 mL, 6.39 mmol) at −78° C., then it was warmed up to room temperature and stirred at room temperature for 2 h, the solution was diluted with DCM, washed with Sat. NaHCO$_3$, brine, dried and concentrated to give ethyl 5-(((trifluoromethyl)sulfonyl)oxy)-3,6-dihydro-2H-pyran-4-carboxylate as crude product (2 g).

Step 2:

To a solution of ethyl 5-(((trifluoromethyl)sulfonyl)oxy)-3,6-dihydro-2H-pyran-4-carboxylate (crude from step 1) and 1-isopropyl-5-(4,4,5,5-tetramethyl-1,3,2-dioxaborolan-2-yl)-1H-pyrazole (1.37 g, 5.82 mmol) in dioxane (20 ml) was added Pd(dppf)Cl$_2$ (430 mg, 0.58 mmol) and Na$_2$CO$_3$ (1.85 g, 17.46 mmol) in water (6 mL), the mixture was degased with N2 for 5 min, and was heated at 100° C. for 15 h, after cooling to room temperature the mixture was diluted with EtOAc and washed with Sat. NaHCO$_3$ and brine, organic layer was combined, dried and concentrated to give crude product, which was purified by column chromatography (Hexanes/EtOAc=3:1) to give ethyl 5-(1-isopropyl-1H-pyrazol-5-yl)-3,6-dihydro-2H-pyran-4-carboxylate (850 mg).

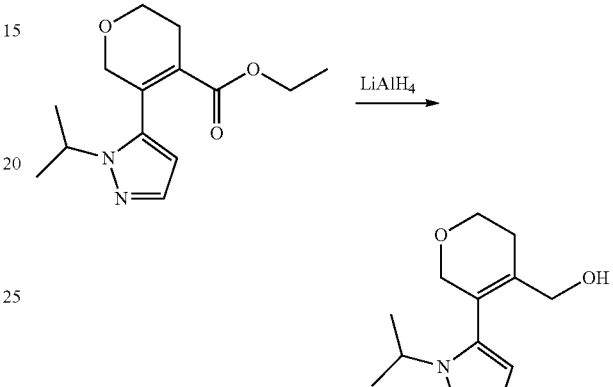

Step 3:

To a solution of ethyl 5-(1-isopropyl-1H-pyrazol-5-yl)-3,6-dihydro-2H-pyran-4-carboxylate (600 mg, 2.27 mmol) in THF (10 mL) was added LiAlH$_4$ (1M in THF, 2.72 mL, 2.72 mmol) at −20° C., the reaction was stirred at −20° C. for 30 min, and was quenched with Sat. NH$_4$Cl, the aqueous layer was extracted with EtOAc, the combined organics were washed with brine, dried and concentrated to give crude oil, which was purified by column (Hexanes/EtOAc=100:0 to 20:80) to give (5-(1-isopropyl-1H-pyrazol-5-yl)-3,6-dihydro-2H-pyran-4-yl)methanol (500 mg).

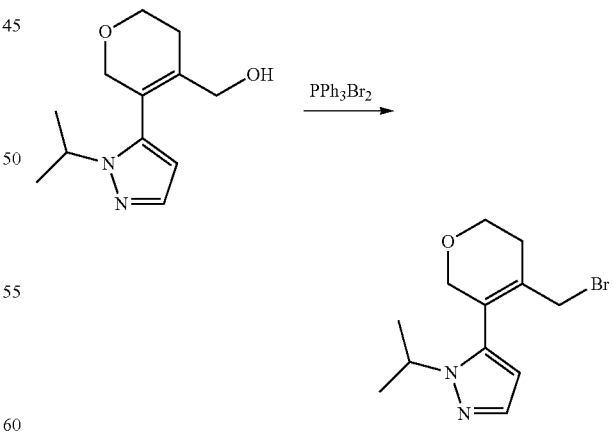

Step 4:

To a solution of (5-(1-isopropyl-1H-pyrazol-5-yl)-3,6-dihydro-2H-pyran-4-yl)methanol (300 mg, 1.35 mmol) in DCM (5 mL) was added dibromotriphenylphosphorane (630 mg, 1.35 mmol) at room temperature, after stirring for 30 min, it was diluted with DCM, organic layer was washed with Sat.

NaHCO₃, brine, dried and concentrated to give crude product, which was purified by column (Hexanes/EtOAc=4:1) to give 5-(4-(bromomethyl)-5,6-dihydro-2H-pyran-3-yl)-1-isopropyl-1H-pyrazole (360 mg).

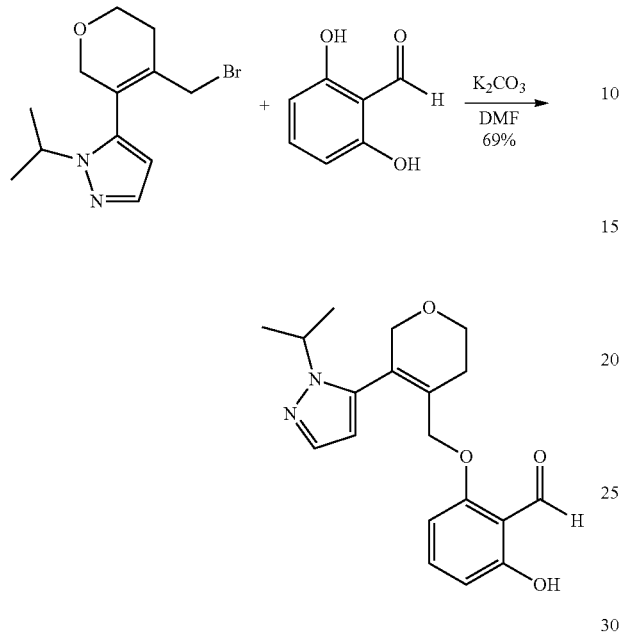

Step 5:

To a solution of 5-(4-(bromomethyl)-5,6-dihydro-2H-pyran-3-yl)-1-isopropyl-1H-pyrazole (110 mg, 0.38 mmol) and 2,6-dihydroxybenzaldehyde (100 mg, 0.76 mmol) in DMF (6 mL) was added K₂CO₃ (110 mg, 0.76 mmol). After stirred at room temperature for 1 h, it was diluted with water and EtOAc, organic layer was separated, and the aqueous layer was extracted with EtOAc. Organic layer was combined, washed with brine, dried and concentrated to give crude product, which was purified by column (Hexanes/EtOAc=1:1) to give 2-hydroxy-6-((5-(1-isopropyl-1H-pyrazol-5-yl)-3,6-dihydro-2H-pyran-4-yl)methoxy)benzaldehyde (90 mg). 1H NMR (400 MHz, CDCl₃) δ (ppm) 11.89 (s, 1H), 10.33 (s, 1H), 7.53 (d, J=1.6 Hz, 1H), 7.33 (t, J=8.8 Hz, 1H), 6.51 (d, J=8.8 Hz, 1H), 6.16 (d, J=8.0 Hz, 1H), 6.08 (d, J=2.0 Hz, 1H), 4.40 (dd, J=12.8, 6.4 Hz, 1H), 4.35 (s, 2H), 4.18 (s, 2H), 3.97 (t, J=5.2 Hz, 2H), 2.44 (s, 2H), 1.40 (d, J=6.4 Hz, 6H); MS (ESI) m/z 343.3 [M+H]⁺.

Example 7

Preparation of 4-((2-(1-isopropyl-1H-pyrazol-5-yl)pyridin-3-yl)methoxy)-2-(methylamino)nicotinaldehyde (compound 21 in Table 1)

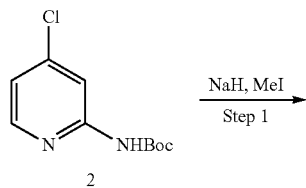

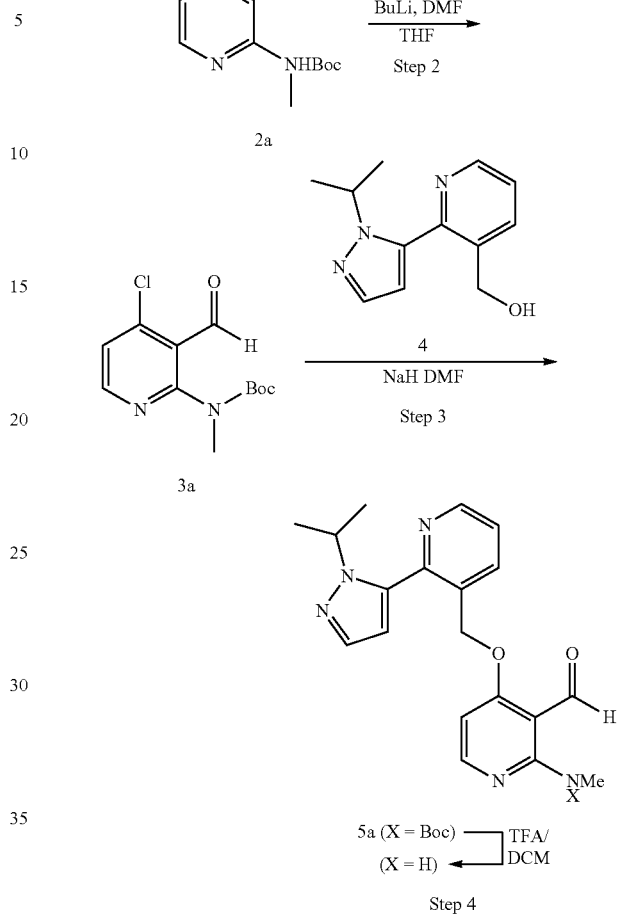

Step 1. Into a 100-mL round-bottom flask, was placed a solution of tert-butyl N-(4-chloropyridin-2-yl)carbamate (3.0 g, 13.12 mmol, 1.00 equiv) in tetrahydrofuran (50 mL). This was followed by the addition of sodium hydride (631 mg, 26.29 mmol, 1.20 equiv) at 0° C. The mixture was stirred for 20 min at 0° C. To this was added iodomethane (2.24 g, 15.78 mmol, 1.20 equiv) dropwise with stirring. The resulting solution was stirred for 6 h at room temperature. The reaction was then quenched by the addition of 30 mL of water. The resulting solution was extracted with 3×30 mL of ethyl acetate and the organic layers combined and concentrated under vacuum. This resulted in 3.01 g (95%) of tert-butyl N-(4-chloropyridin-2-yl)-N-methylcarbamate as a yellow oil.

Step 2. Into a 100-mL three neck round-bottom flask, was placed a solution of tert-butyl N-(4-chloropyridin-2-yl)-N-methylcarbamate (1.5 g, 6.18 mmol, 1.00 equiv) in tetrahydrofuran (50 mL). This was followed by the addition of BuLi (2.5M) (3.0 mL, 1.20 equiv) dropwise with stirring at −78° C. The mixture was stirred for 30 mins at −78° C. To this was added N,N-dimethylformamide (1.5 mL, 3.00 equiv) dropwise with stirring at −78° C. The resulting solution was stirred for 1 h at −78° C. The reaction was then quenched by the addition of 2.5 mL of hydrogen chloride (12M). The resulting mixture was concentrated under vacuum. The residue was dissolved in 40 mL of EA. The resulting mixture was washed with 1×30 mL of 5% sodium bicarbonate and 1×20 mL of brine. The resulting mixture was concentrated under vacuum.

The residue was applied onto a silica gel column with EA:PE (1:4). This resulted in 0.97 g (92%) of 4-chloro-2-(methylamino)pyridine-3-carbaldehyde as a yellow solid.

Steps 3 & 4. Into a 100-mL round-bottom flask, was placed a solution of [2-[1-(propan-2-yl)-1H-pyrazol-5-yl]pyridin-3-yl]methanol (1.15 g, 5.29 mmol, 1.00 equiv) in N,N-dimethylformamide (40 mL). This was followed by the addition of sodium hydride (530 mg, 13.25 mmol, 2.50 equiv, 60%) at 0° C. The mixture was stirred for 15 min at 0° C. To this was added 4-chloro-2-(methylamino)pyridine-3-carbaldehyde (900 mg, 5.28 mmol, 1.00 equiv). The resulting solution was stirred overnight at room temperature. The reaction was then quenched by the addition of 30 mL of water. The resulting solution was extracted with 5×30 mL of ethyl acetate and the organic layers combined and concentrated under vacuum. The crude product (300 mg) was purified by Prep-HPLC with the following conditions (Prep-HPLC-020): Column, SunFire Prep C18 OBD Column, 5 um, 19*100 mm, mobile phase, water with 0.1% TFA and MeCN (3.0% MeCN up to 20.0% in 5 min, up to 95.0% in 2 min, down to 3.0% in 1 min); Detector, waters 2489 254&220 nm. This resulted in 107.1 mg (6%) of 2-(methylamino)-4-([2-[1-(propan-2-yl)-1H-pyrazol-5-yl]pyridin-3-yl]methoxy)pyridine-3-carbaldehyde as a yellow solid. $^1$HNMR (400 MHz, DMSO, ppm): 8.72 (m, 1H), 8.17 (s, 1H), 7.91 (m, 1H), 7.52 (m, 3H), 6.56 (s, 1H), 6.26 (d, J=4.2 Hz, 1H), 6.15 (d, J=3.3 Hz, 1H), 5.43 (m, 1H), 5.12 (m, 1H), 4.60 (m, 1H), 2.87 (d, J=3.3 Hz, 1H), 1.46 (d, J=5.1 Hz, 1H), 1.35 (d, J=5.1 Hz, 1H); (ES, m/z): 352.1 [M+1]$^+$ Example 8

Preparation of N-(1-ethyl-1H-pyrazol-5-yl)-2-(2-formyl-3-hydroxyphenoxy)-N-isopropylacetamide (compound 22 in Table 1)

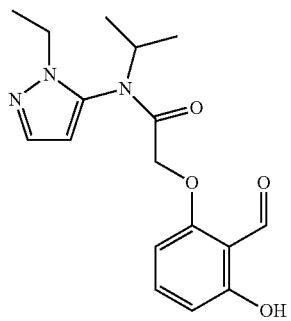 [SMILES: CCn1nccc1N(C(=O)COc1cccc(O)c1C=O)C(C)C]

Step 1

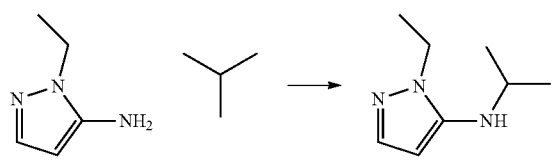

1-Ethyl-1H-pyrazol-5-amine (0.7 g, 6.3 mmol) was dissolved in THF (5 ml). Sodium hydride (0.5 g, 60% dispersion in mineral oil, 12.6 mmol) was added and the mixture stirred for 10 m. 2-iodopropane (0.82 g, 8.2 mmol) was added and the mixture stirred for 16 h. Water (50 ml) and ethyl acetate (100 ml) were added. The phases were separated and the aqueous phase was extracted with ethyl acetate (2×75 ml). The combined organic phases were washed with a saturated aqueous sodium chloride solution (30 ml) and then dried over sodium sulfate. After evaporation, the residue was purified by silica gel chromatography (5-50% ethyl acetate/hexanes) to give 0.49 g (50%) of 1-ethyl-N-isopropyl-1H-pyrazol-5-amine as a yellowish oil. MS (ESI) m/z 154 [M+H]$^+$.

Step 2

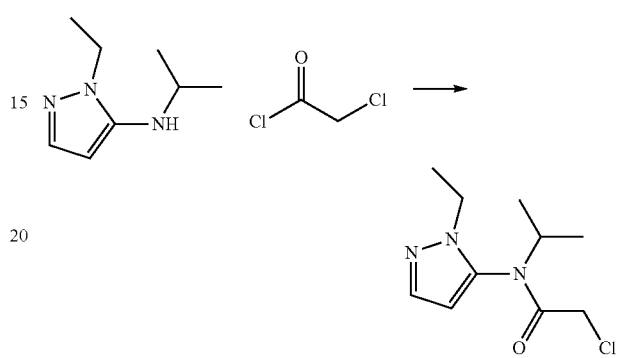

1-Ethyl-N-isopropyl-1H-pyrazol-5-amine (0.49 g, 3.2 mmol) was dissolved in dichloromethane (11 ml) and stirred in an ice bath. N,N-diisopropylethylamine (1.14 ml, 6.4 mmol) was added followed by slow addition of chloroacetyl chloride (0.51 ml, 6.4 mmol). The reaction was stirred to 25° C. over 16 h. Water (100 ml) and ethyl acetate (100 ml) were added and the phases were separated. The aqueous phase was extracted with ethyl acetate (2×50 ml) and the combined organic phases were washed with a saturated aqueous sodium chloride solution (25 ml). After drying over sodium sulfate and evaporation the residue was purified by silica gel chromatography (5-80% ethyl acetate/hexanes) to give 0.39 g (53%) of 2-chloro-N-(1-ethyl-1H-pyrazol-5-yl)-N-isopropylacetamide as a brownish solid. MS (ESI) m/z 230 [M+H]$^+$.

Step 3

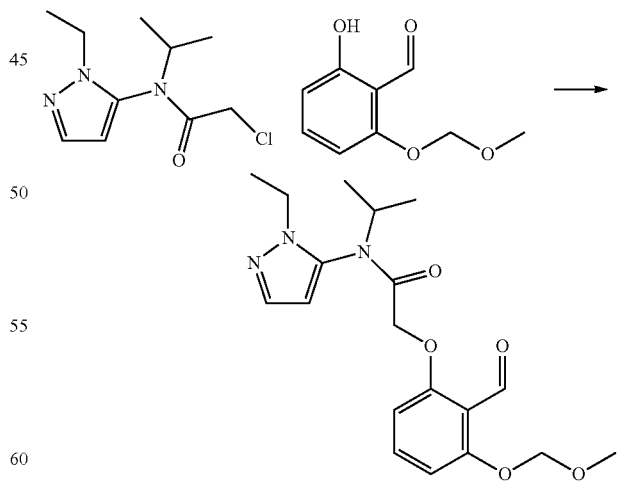

2-Chloro-N-(1-ethyl-1H-pyrazol-5-yl)-N-isopropylacetamide (0.39 g, 1.7 mmol) and 2-hydroxy-6-(methoxymethoxy)benzaldehyde (0.309 g, 1.7 mmol) were dissolved in DMF (8.5 ml) and purged with N$_2$ gas. Potassium carbonate (0.47 g, 3.4 mmol) was added and the mixture was stirred in a heat block at 60° C. After 2 h, the reaction was cooled and partitioned into ethyl acetate (100 ml) and water (100 ml). The phases were separated and the aqueous phase was extracted with ethyl acetate (2×50 ml). The combined organic phases were washed with water (50 ml) and a saturated aqueous sodium chloride solution (50 ml), and dried over sodium sulfate. After evaporation the residue was purified by silica gel chromatography (5-50% ethyl acetate/hexanes) to give 0.38 g (59%) of N-(1-ethyl-1H-pyrazol-5-yl)-2-(2-formyl-3-(methoxymethoxy)phenoxy)-N-isopropylacetamide as a faintly-colored viscous oil. MS (ESI) m/z 376 [M+H]$^+$.

Step 4

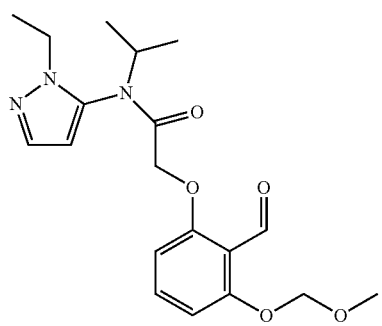

N-(1-Ethyl-1H-pyrazol-5-yl)-2-(2-formyl-3-(methoxymethoxy)phenoxy)-N-isopropylacetamide (0.38 g, 1.01 mmol) was dissolved in THF (10 ml), purged with N$_2$ gas and stirred in an ice bath. HCl (concentrated, 0.34 ml, 4.05 mmol) was slowly added and the solution stirred to 25° C. More HCl (0.3 ml) was added over 4 h with warming (40° C.) to reach completion of reaction. 10% Sodium bicarbonate solution (20 ml) was added and the mixture was extracted with ethyl acetate (3×75 ml). The combined organic phases were washed with a saturated aqueous sodium chloride solution (50 ml) and dried over sodium sulfate. After evaporation the resulting solid was purified by silica gel chromatography (5-80% ethyl acetate/hexanes) to give 0.179 g (53%) of N-(1-ethyl-1H-pyrazol-5-yl)-2-(2-formyl-3-hydroxyphenoxy)-N-isopropylacetamide as a white solid. $^1$H NMR (400 MHz, CDCl$_3$) δ 11.90 (s, 1H), 10.35 (s, 1H), 7.50 (s, 1H), 7.43 (t, J=8.43 Hz, 1H), 6.67 (d, J=8.53 Hz, 1H), 6.39 (d, J=8.27 Hz, 1H), 6.32-6.27 (m, 1H), 6.12 (d, J=7.30 Hz, 1H), 5.65 (s, 1H), 4.25-4.13 (m, 3H), 1.46 (t, J=7.23 Hz, 3H), 1.22 (d, J=6.54 Hz, 3H), 1.14 (d, J=6.51 Hz, 3H). MS (ESI) m/z 332 [M+H]$^+$. MP 179-182° C.

Example 9

Preparation of 2-(((2-(1-isopropyl-1H-pyrazol-5-yl)pyridin-3-yl)oxy)methyl)benzaldehyde (compound 23 in Table 1)

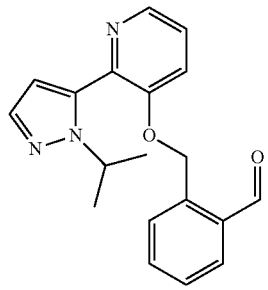 [SMILES: CC(C)n1nccc1-c1ncccc1OCc1ccccc1C=O]

The compound was prepared from ethyl 2-(bromomethyl)benzonitrile in 2 steps according to reaction scheme below.

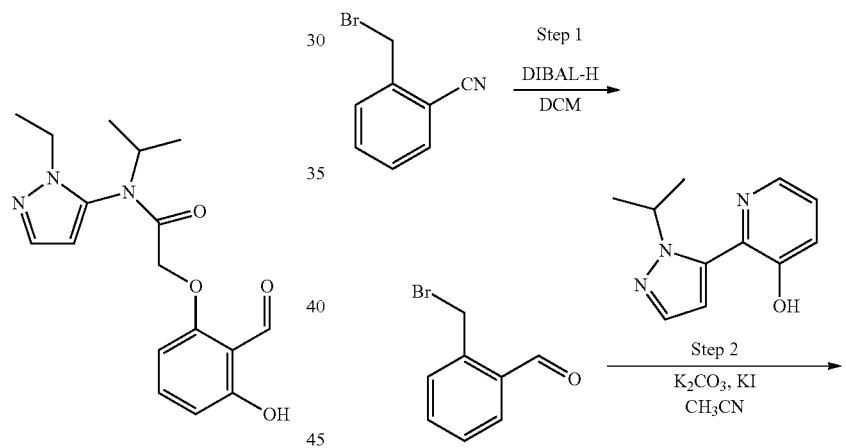

Step 1.

Into a 100-mL round-bottom flask, was placed a solution of 2-(bromomethyl)benzonitrile (1.0 g, 5.10 mmol, 1.00 equiv) in dichloromethane (40 mL). This was followed by the addition of DIBAL-H (5.5 mL, 1.10 equiv) at 0° C. The resulting solution was stirred for 3.5 h at 0° C. The reaction was then quenched by the addition of 10 mL of 5% HBr at 0° C. The resulting solution was extracted with 3×30 mL of dichloromethane and the combined organic layers were dried over anhydrous sodium sulfate. The residue was applied onto a silica gel column with ethyl acetate/petroleum ether (1:10) as eluent. This resulted in 500 mg (49%) of 2-(bromomethyl)benzaldehyde as a green oil.

Step 2.

Into a 50-mL round-bottom flask, was placed a solution of 2-(bromomethyl)benzaldehyde (150 mg, 0.75 mmol, 1.00 equiv) in $CH_3CN$ (25 mL). 2-[1-(Propan-2-yl)-1H-pyrazol-5-yl]pyridin-3-ol (150 mg, 0.74 mmol, 1.00 equiv), potassium carbonate (210 mg, 1.52 mmol, 2.00 equiv), and KI (40 mg, 0.30 equiv) were added to the reaction. The resulting solution was heated to reflux for 6 h, and then it was cooled to rt. The resulting solution was diluted with 20 mL of $H_2O$, and then it was extracted with 3×20 mL of ethyl acetate. The combined organic layers were washed with 1×30 mL of brine and concentrated under vacuum. The crude product (200 mg) was purified by Prep-HPLC with the following conditions (Prep-HPLC-010): Column, SunFire Prep C18 OBD Column, 5 um, 19*150 mm, mobile phase, water with 0.05% TFA and MeCN (38.0% MeCN up to 55.0% in 8 min); Detector, nm. This provided 98.6 mg (41%) of 2-[([2-[1-(propan-2-yl)-1H-pyrazol-5-yl]pyridin-3-yl]oxy)methyl]benzaldehyde as a light yellow solid; $^1$HNMR (300 MHz, $CDCl_3$, ppm): 10.01 (s, 1H), 8.43 (m, 1H), 7.88 (m, 1H), 7.86 (m, 1H), 7.61-7.79 (m, 6H), 6.61 (d, J=2.1 Hz, 1H), 5.60 (s, 2H), 4.69-4.78 (m, 1H), 1.46 (d, J=6.6 Hz, 6H); (ES, m/z): 322 $[M+1]^+$.

Adduct Formation

Example 10

Purification of Human Oxyhemoglobin S (oxyHbS)

After purification, oxyHbS was dialyzed against 20 mM HEPES-HCl (pH 6.8) and concentrated using Millipore centrifugal concentrators. The highly concentrated (around 300 mg/ml) small volume aliquots of pure oxyHbS were flash-frozen in liquid nitrogen and stored in liquid nitrogen until use. All chemicals (biochemical grade or greater quality) unless custom made were purchased from Sigma-Aldrich (St. Louis, Mo., USA). Carbon monoxide (pure grade) was obtained from TechAir (White Planes, N.Y., USA).

As shown in FIG. 1, the ESI-MS spectrum of human hemoglobin S (betaE6V) shows that human HbS consists of a typical alpha A globin subunit (molecular mass of 15,126 Da) and a mutant (betaE6V) beta S globin subunit (molecular mass of 15,837 Da).

Example 11

Mass-Spectroscopy of oxyHbS

The HbS protein sample (~10 mg/ml) was diluted 1:10 or 1:100 in 50% acetonitrile-0.1% formic acid. Electrospray mass spectrometry (ESI-MS) was performed on a linear trap quadruple (LTQ) ion trap mass spectrometer (Thermo Fisher Scientific, San Jose, Calif.). The diluted samples were infused at flow rates of 5 µl/min. ESI-MS experimental results are presented in FIG. 1.

Example 12

Preparation of Human Carbonmonoxyhemoglobin S (COHbS) and Monitoring of Iron Oxidation The samples of oxyHbS were thawed at room temperature and then diluted with 20 mM HEPES buffer (pH 7.1 or 7.4) to achieve a final protein concentration of 10 to 12 mg/ml. The diluted oxyHbS, in aliquots of 100 µl, were exposed to carbon monoxide (CO) gas flow for at least 1 minute without bubbling. All crystallization solutions were treated by bubbling CO gas through them for a few minutes. The CO saturation level in hemoglobin preparations was estimated based on differences between absorption spectra of oxyHbS and COHbS. The CO saturation level in COHbS preparations was maintained at the level of greater than 95% during all manipulations including crystallization. The presence of methemoglobin S (with iron oxidized to the +3 state) in all experiments was monitored visually (for instance, by observing crystals changing color from bright red to dark brown), and spectroscopically by monitoring absorbance of hemoglobin solutions at λ=630 nm (the differences between absorption spectra are explained in FIG. 2 and Table 2). The liganded status of hemoglobin S was further confirmed by determining its crystal structure.

Figure 2:
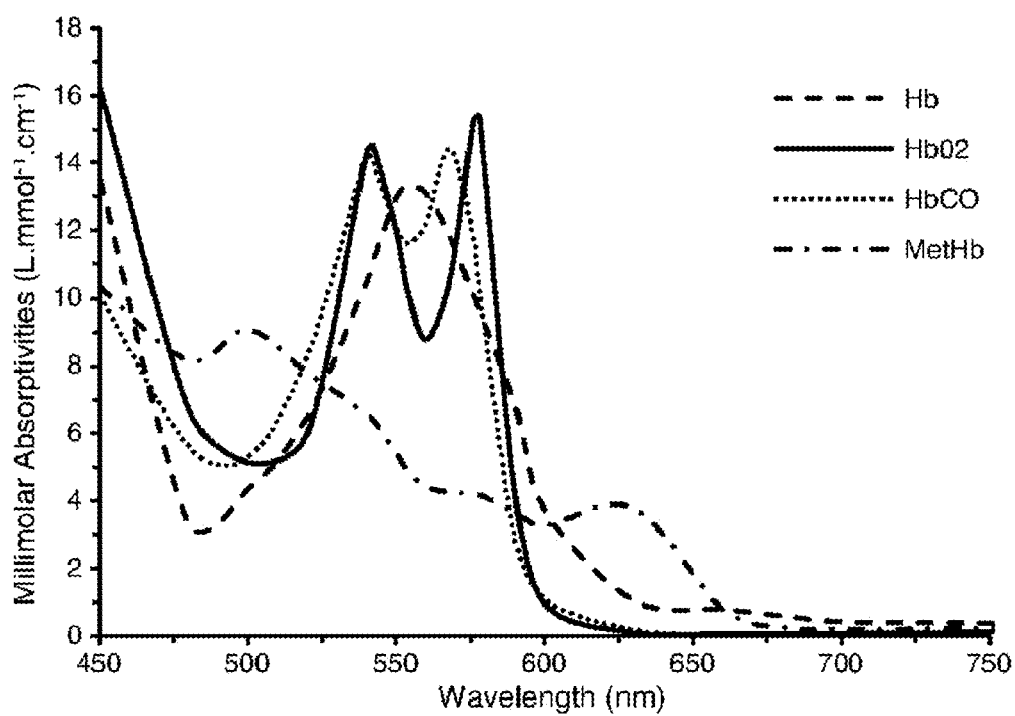
FIG. 2 depicts absorption spectra for four ligand states of human adult hemoglobin A.

Shown in FIG. 2 are absorption spectra for four ligand states of human adult hemoglobin A. (from Zijlstra W. G., et al., Absorption-spectra of human fetal and adult oxyhemoglobin, de-oxyhemoglobin, carbonmonoxyhemoglobin, and methemoglobin. *Clin. Chem.* 37, (9), 1633-1638 (1991). 0009-9147)

Absorption parameters for human hemoglobin A are shown in Table 2. The wavelength (λ) in nanometers for each maximum is followed by the extinction coefficient (ε) placed in parentheses. (From: O. W. Van Assendelft. Spectrophotometry of Hemoglobin Derivatives, Royal Vangorcum, Ltd., Assen, The Netherlands and Charles C Thomas, Springfield, Ill. 1970, 152 pp.)

TABLE 2

| Term | Symbol | Absorption peak 1 | | Absorption peak 2 | | Absorption peak 3 | |
|---|---|---|---|---|---|---|---|
| | | λ | ε | λ | ε | λ | ε |
| Deoxyhemoglobin | Hb | 431 | (140) | 555 | (13.04) | | |
| Oxyhemoglobin | $HbO_2$ | 415 | (131) | 542 | (14.37) | 577 | (15.37) |
| Carbonmonoxyhemoglobin | HbCO | 420 | (192) | 539 | (14.36) | 568.5 | (14.31) |
| Hemiglobin (methemoglobin) | MetHb | 406 | (162) | 500 | (9.04) | 630 | (3.70) |

Example 13

Figure 3:
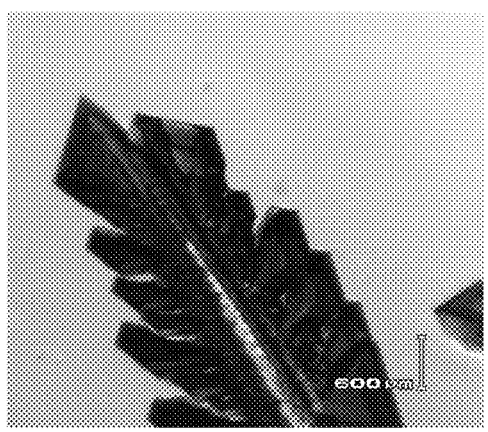
FIG. 3A illustrates "COHbS crystal clusters" and 3B illustrates "large COHbS monocrystals" as described in the Examples below.
Figure 3:
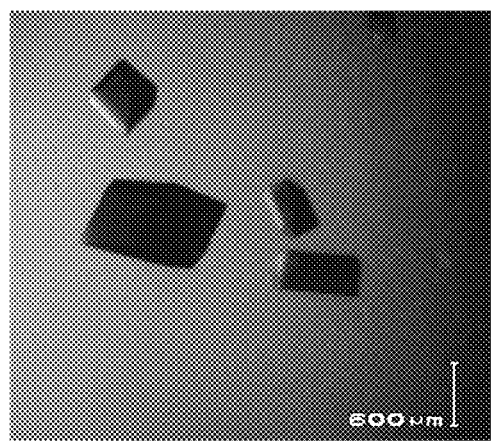

Crystallization of Human Carbonmonoxyhemoglobin S (betaE6V) without Cryoprotectants Human COHbS was crystallized as described previously (Patskovska L N, Patskovsky Y V, Almo S C, Hirsch R E. COHbC and COHbS crystallize in the R2 quaternary state at neutral pH in the presence of PEG 4000, Acta Crystallogr D Biol Crystallogr. 2005 May; 61(Pt 5):566-73.) by a sitting drop vapor diffusion method with some modifications. In brief, 3 μl or 5 μl of a freshly prepared COHbS (10-12 mg/ml) solution in 20 mM HEPES (pH 7.1 or pH 7.4) was mixed with an equal volume of a precipitant solution containing 100 mM HEPES (pH 7.1 or pH 7.4), 20-30% (v/v) PEG 4000 and 10-60 mM of sodium chloride in 24-well Cryschem crystallization plates (Hampton Research, Aliso Viejo, Calif., USA) and equilibrated against 0.5 ml or 1 ml of a precipitant solution at room temperature (294° K) for 1-14 days. The appearance of hemoglobin crystals was monitored visually and microscopically every 48-72 hours after beginning of the experiments. The precipitant solution was pre-treated with carbon monoxide (by bubbling CO gas through it for a few minutes), and it was replaced at least every two weeks plus every time the crystallization chamber was opened for manipulations and exposed to air. More concentrated precipitant solutions containing 26-30% PEG 4000 were used to produce protein crystals that grew up fast, in about 3 days. However, the "fast-growing" COHbS crystals were either relatively small or appeared as crystal clusters (FIG. 3A). On the other hand, the "fast-growing" crystals were less likely to contain a detectable amount of methemoglobin and usually diffracted better than crystals "older" than 10-14 days. To produce the very large (up to 1-2 mm in length) COHbS mono-crystals, less concentrated precipitant solutions with 20-24% PEG 4000 and much longer crystallization time (around 10-14 days) were used. For X-ray diffraction experiments performed at room temperature we have produced large COHbS monocrystals as they diffracted to higher resolution (an example in shown in FIG. 3B). However, growing large mono-crystals was a time consuming process, less suited for high throughput screening experiments. In most cases, COHbS crystal clusters (FIG. 3A) were carefully "broken" and separated into individual crystals either manually or by soaking them into a precipitant solution supplemented with 10-20% of glycerol or ethylene glycol. Shown in FIG. 3 are photographs of COHbS crystal cluster grown in the presence of 26% PEG4000 for 4 days (A) and single hemoglobin monocrystals grown in the presence of 20% PEG4000 for 14 days (B).

Example 14

Cryoprotection of COHbS Crystals and Crystallization in the Presence of Cryoprotectants The COHbS crystals obtained without additional cryoprotectants were not suitable for direct freezing and required a special treatment with selected cryoprotectants before being subjected to flash freezing in liquid nitrogen. Yet another approach for producing frozen COHbS crystals was to introduce a cryoprotectant directly in a precipitant solution during protein crystallization. Again, all solutions that were used for growing and handling COHbS crystals were saturated with carbone monoxide gas.

For cryoprotection, the already grown COHbS crystals were soaked in a precipitant solution supplemented with glycerol (10-30%, v/v), or ethyleneglycol (15-30%, v/v) or dimethylsulfoxide (15-25%, v/v). Among the tested cryoprotectants the most efficient was glycerol, which was well-tolerated by COHbS crystals not only as a cryoprotectant but also as an additive in crystallization. Pure paraffin oil (Hampton Research) did not act as a cryoprotectant but it did not destroy the COHbS crystals during an incubation time of up to 2 hours. This feature was convenient and 2-3 μl of paraffin oil was occasionally used to cover up and thus prevent evaporation of a crystallization drop thus reducing any possibility for gas exchange in the process of soaking COHbS crystals in solutions with different additives.

During cryoprotection, the COHbS crystals were soaked in for a short time (3-10 minutes) or much longer (up to 72 hours). The short soaking time was used for testing cryoconditions and for quick freezing of hemoglobin crystals. The longer soaking time (from 30 minutes to 3 days) was used when the COHbS crystals were incubated in the presence of slow reacting and/or low water-soluble compounds. For the tested compounds that were not very soluble in water and water-based solutions, an overnight or even longer incubation time was used to produce protein-ligand complexes.

Figure 4:
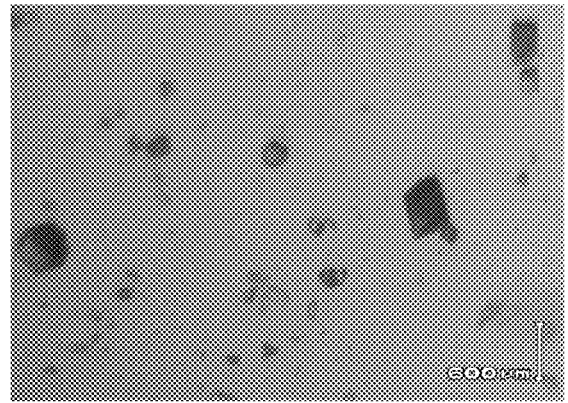
FIG. 4 illustrates "secondary COHbS protein crystals" incubated in the presence of glycerol, as described in the Examples below.

Often when COHbS crystals were incubated in the presence of glycerol, new ("secondary") protein crystals grew (FIG. 4). These smaller crystals, together with "soaked" crystals, were frozen directly in liquid nitrogen and used to determine and compare crystal structures of COHbS obtained by both soaking and co-crystallization in identical conditions.

As shown in FIG. 4, the COHbS single mono-crystals grew in the presence of 15% glycerol (v/v) in 24 hours. The crystallization drop was initially equilibrated for 4 days against a precipitant containing 26% PEG4000 and had a large crystal cluster (FIG. 3). Glycerol was gradually added (with a 5% increment) to the crystallization drop and to the precipitant chamber. The small amount of a tested compound GBT210 (dry powder, which is seen as gray dots) was also added to the crystallization drop as well. These crystals were frozen directly in liquid nitrogen and used to determine the structure of the COHbS-GBT210 complex.

The ability of the "secondary" crystals to grow after adding glycerol to the crystallization drops provides a crystallization strategy for producing "ready-to-freeze" COHbS crystals. In such experiments the crystallization drops were set up as described in a previous chapter except for the presence of 10% to 20% (v/v) glycerol in a precipitant solution. The PEG4000 concentration, however, was slightly lower and varied between 18 and 26%. The advantage of this method was that the protein crystals grown in the presence of glycerol were frozen directly in liquid nitrogen bypassing any extra treatments/manipulations.

Example 15

Producing Protein-Ligand Complexes by Soaking COHbS Crystals in a Ligand Suspension or Solution and by Co-Crystallization Each tested compound was suspended either in 20 mM HEPES (for co-crystallization studies) or in a precipitant solution (for crystal soaking experiments) in order to produce a saturated compound solution. Among tested chemicals, only few were very water-soluble, so saturated solutions were used and serial 1:10 dilutions (1:10, 1:100 and 1:1000) in the subsequent crystal soaking and co-crystallization experiments. For soaking, a saturated solution (or its serial dilutions) of each compound was added to the crystallization drops with COHbS crystals (in a ratio of 1:1 volume/volume). After overnight incubation, the COHbS crystals were briefly soaked in a precipitant solution supplemented with 15% or 20% of either glycerol or ethylene glycol as cryoprotectants and flash-frozen in liquid nitrogen.

In other experiments, COHbS was crystallized in the presence of 10% or 20% glycerol. A tested compound was added to the crystallization drops and after incubation the COHbS crystals were frozen directly in liquid nitrogen.

In co-crystallization experiments, the ligand was gently mixed with COHbS stock solution (20-24 mg/ml) before setting up crystallization drops. When the hemoglobin crystals grew, they were treated with a cryoprotectant as described above and frozen in liquid nitrogen. When the crystals were grown in the presence of glycerol, they were frozen directly without any additional treatment.

In a separate experiment, certain less water-soluble organic compounds were dissolved in 100% DMSO and then diluted (1:1) with either a precipitant solution or 20 mM HEPES (pH 7.4) buffer. The insoluble fraction was removed by sedimentation or centrifugation and the resulting solutions were used in soaking and in co-crystallization experiments as well. The final concentration of DMSO in the crystallization drops varied between 10 and 25%. After incubation, the protein crystals were flash frozen in liquid nitrogen and stored until use.

Example 16

X-Ray Diffraction Data Collection, Structure Solution and Refinement

X-ray diffraction data from flash-cooled crystals were collected on the beam line X29A of the National Synchrotron Light Source (Brookhaven National Laboratory, New York) equipped for the rapid data collection studies and using a radiation wavelength (λ) of 1.075 Å and a CBASS data collection software. A few X-ray diffraction data sets were also collected at the beam line 31ID at the Advanced Photon Source (Argonne National Laboratory, IL, USA) using a wavelength of 0.9793 Å. The room temperature X-ray diffraction experiments were performed on crystals mounted inside the standard MiTeGen plastic capillaries (MiTeGen, Ithaca, N.Y., USA). The room temperature diffraction data were collected at a wavelength of 1.5418 Å using a RIGAKU Cu rotating anode as an X-ray generator and an RAXIS IV image plate area detector. (An attempt to collect room temperature diffraction data at X29A was unsuccessful due to extensive crystal damage). All collected X-ray diffraction data were processed and scaled using the HKL (2000 or 3000) software packages (Z. Otwinowski, M. Minor. Processing of X-ray diffraction data collected in oscillation mode. Methods Enzymol., 276 (1997), pp. 307-326). The crystal structures were determined by molecular replacement method using PHASER software (CCP4 program package, M. D. Winn et al. Overview of the CCP4 suite and current developments. Acta. Cryst. D67, 235-242 (2011)) and coordinates of the PDB file 1NEJ as a search model. Refinement was performed with REFMAC (G. N. Murshudov, A. A. Vagin and E. J. Dodson. Refinement of Macromolecular Structures by the Maximum-Likelihood method. Acta Cryst. D53, 240-255 (1997). Errors in the model corrected manually using COOT visualization and refinement graphic interface (P. Emsley, K. Cowtan. Coot: model-building tools for molecular graphics. Acta Crystallogr., D60 (2004), pp. 2126-2132). The CIF files for novel compounds were created using SKETCHER (CCP4 program package) and fixed manually when needed.

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entirety.

What is claimed is:

1. A method for increasing oxygen affinity of sickle hemoglobin (HbS) in vivo in a patient in need thereof which method comprises administering to said patient a sufficient amount of 2-(((2-(1-isopropyl-1H-pyrazol-5-yl)pyridin-3-yl)oxy)methyl)-6-hydroxybenzaldehyde or a salt thereof such that said 2-4(2-(1-isopropyl-1H-pyrazol-5-yl)pyridin-3-yl)oxy)methyl)-6-hydroxybenzaldehyde or a salt thereof binds to HbS to form a 1:1 adduct in vivo and further wherein said adduct increases the oxygen affinity of said HbS.

2. A method for inhibiting sickling of HbS in a patient which method comprises administering to said patient a sufficient amount of a composition comprising 2-(((2-(1-isopropyl-1H-pyrazol-5-yl)pyridin-3-yl)oxy)methyl)-6-hydroxybenzaldehyde or a salt thereof such that said 2-(((2-(1-isopropyl-1H-pyrazol-5-yl)pyridin-3-yl)oxy)methyl)-6-hydroxybenzaldehyde or a salt thereof binds to HbS to form, in vivo, a 1:1 adduct thereby inhibiting sickling of HbS.

* * * * *